(12) United States Patent
Zhang

(10) Patent No.: US 8,637,545 B2
(45) Date of Patent: Jan. 28, 2014

(54) PIPERIDINE-2, 6-DIONE DERIVATIVES AND THEIR USE AS TUMOR NECROSIS FACTOR INHIBITORS

(75) Inventor: Hesheng Zhang, Tianjin (CN)

(73) Assignee: Tianjin Hemay Bio-Tech Co., Ltd., Tianjin (CN)

( * ) Notice: Subject to any disclaimer, the term of this patent is extended or adjusted under 35 U.S.C. 154(b) by 1509 days.

(21) Appl. No.: 11/868,502

(22) Filed: Oct. 7, 2007

(65) Prior Publication Data

US 2008/0051432 A1    Feb. 28, 2008

Related U.S. Application Data

(63) Continuation of application No. PCT/CN2005/001467, filed on Sep. 13, 2005.

(30) Foreign Application Priority Data

Apr. 7, 2005   (CN) .......................... 2005 1 0013292

(51) Int. Cl.
    *A61K 31/454*   (2006.01)
    *C07D 403/14*   (2006.01)
(52) U.S. Cl.
    USPC .......................................... 514/323; 546/201
(58) Field of Classification Search
    USPC .......................................... 514/323; 546/201
    See application file for complete search history.

(56) References Cited

U.S. PATENT DOCUMENTS

| | | | | |
|---|---|---|---|---|
| 4,163,058 | A * | 7/1979 | Stella et al. | 514/391 |
| 4,709,042 | A * | 11/1987 | Mai et al. | 548/319.1 |
| 5,635,517 | A * | 6/1997 | Muller et al. | 514/323 |
| 6,403,613 | B1 * | 6/2002 | Man et al. | 514/323 |
| 7,741,342 | B2 * | 6/2010 | Zhang | 514/323 |

FOREIGN PATENT DOCUMENTS

WO   WO02068414   * 9/2002

OTHER PUBLICATIONS

Hess et al. "synthesis and immunological . . . " Gioorg. Med. chem. 9, p. 1279-1291 (2001).*
Bundgaard et al. "prodrugs as . . . " CA 93:79967 (1980).*

* cited by examiner

*Primary Examiner* — Celia Chang
(74) *Attorney, Agent, or Firm* — Matthias Scholl P.C.; Matthias Scholl

(57) ABSTRACT

This invention is directed to derivatives of piperidine-2,6-dione, or their organic or inorganic salts thereof, a methods of synthesis of these derivatives, and their application as active pharmaceutical ingredient as inhibitors of TNFα releasing in cells, the derivative of piperidine-2,6-dione being of the general formula (I):

(I)

wherein n represents 1, 2, 3, 4, 5 or 6; $R^1$ represents from one to four of the same or different substituents selected from F, Cl, Br, $C_{1-4}$ alkyl, OH, $OC_{1-4}$ alkyl, $NO_2$, $NHC(O)C_{1-4}$ alkyl, $NH_2$, $NH(C_{1-4}$ alkyl), $N(C_{1-4}$ alkyl)$_2$; $R^2$ represents $OR^3$, $NR^3R^4$, $N(R^3)COR^4$, $O_2CR^5$; $R^3$ and $R^4$ represent independently and at each occurrence H or $C_{1-4}$ alkyl; $R^5$ represents $CHR^6NR^7R^8$, $CHR^6NR^9C(O)CHR^{10}NR^7R^8$, a heterocycle W or $CHR^6NR^9C(O)W$; $R^6$, $R^9$, $R^{10}$ represent independently and at each occurrence H, or $C_{1-4}$ alkyl; $R^7$ and $R^8$ represent independently and at each occurrence H, $C_{1-4}$ alkyl, or $R^7$ and $R^8$ taken together represent 1,3-propylene, 1,4-butylene, 1,5-pentylene, or 1,6-hexylene; W represents four-membered, five-membered, six-membered, seven-membered, or eight-membered saturated or unsaturated heterocycle.

17 Claims, 11 Drawing Sheets

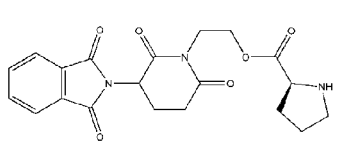

2-(1-(2-hydroxyethyl)-2,6-dioxopiperidin-3-yl)isoindolin-1,3-dione (*S*)-2-pyrrolidinecarboxylate

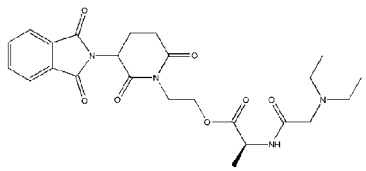

2-(1-(2-hydroxyethyl)-2,6-dioxopiperidin-3-yl)isoindolin-1,3-dione (*S*)-2-(2-diethylaminoacetamido)propanoate

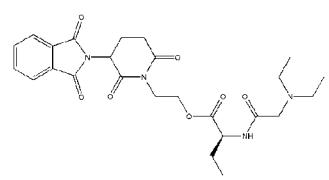

2-(1-(2-hydroxyethyl)-2,6-dioxopiperidin-3-yl)isoindolin-1,3-dione (*S*)-2-(2-diethylaminoacetamido)-3-methylbutanoate

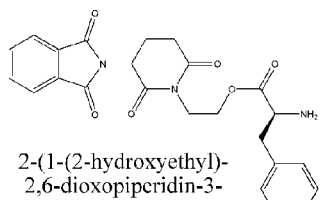

2-(1-(2-hydroxyethyl)-2,6-dioxopiperidin-3-yl)isoindolin-1,3-dione (*S*)-2-amino-3-phenylpropanoate

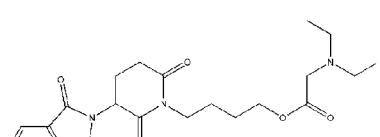

2-(1-(4-hydroxybutyl)-2,6-dioxopiperidin-3-yl)isoindolin-1,3-dione 2-(diethylamino)acetate

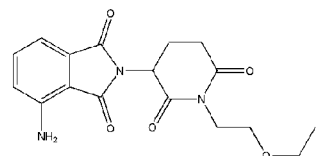

4-amino-2-(1-(2-ethoxyethyl)-2,6-dioxopiperidin-3-yl)isoindoline-1,3-dione

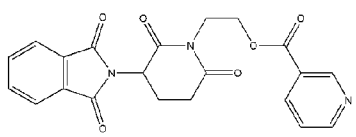

2-(1-(2-hydroxyethyl)-2,6-dioxopiperidin-3-yl)isoindolin-1,3-dione nicotinate

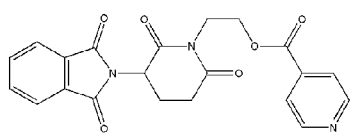

2-(1-(2-hydroxyethyl)-2,6-dioxopiperidin-3-yl)isoindolin-1,3-dione isonicotinate

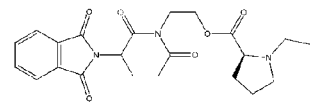

2-(1-(2-hydroxyethyl)-2,6-dioxopiperidin-3-yl)isoindolin-1,3-dione N-ethyl-(*S*)-2-pyrrolidinecarboxylate

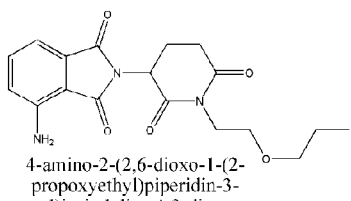

4-amino-2-(2,6-dioxo-1-(2-propoxyethyl)piperidin-3-yl)isoindoline-1,3-dione

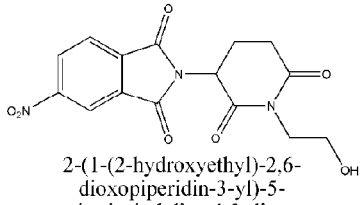

2-(1-(2-hydroxyethyl)-2,6-dioxopiperidin-3-yl)-5-nitroisoindoline-1,3-dione

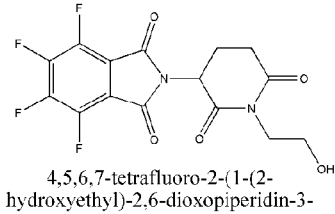

4,5,6,7-tetrafluoro-2-(1-(2-hydroxyethyl)-2,6-dioxopiperidin-3-yl)isoindoline-1,3-dione

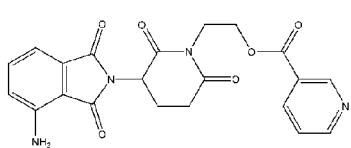

4-amino-2-(1-(2-hydroxyethyl)-2,6-dioxopiperidin-3-yl)isoindolin-1,3-dione nicotinate

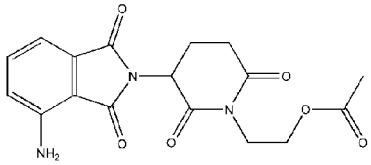

4-amino-2-(1-(2-hydroxyethyl)-2,6-dioxopiperidin-3-yl)isoindolin-1,3-dione acetate

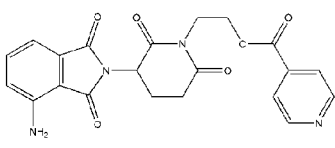

4-amino-2-(1-(2-hydroxyethyl)-2,6-dioxopiperidin-3-yl)isoindolin-1,3-dione isonicotinate

Fig. 2

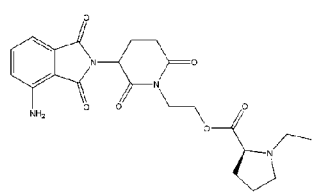
4-amino-2-(1-(2-hydroxyethyl)-2,6-dioxopiperidin-3-yl)isoindolin-1,3-dione N-ethyl-(S)-2-pyrrolidinecarboxylate

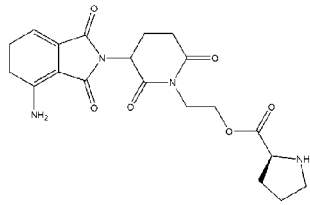
4-amino-2-(1-(2-hydroxyethyl)-2,6-dioxopiperidin-3-yl)isoindolin-1,3-dione (S)-2-pyrrolidinecarboxylate

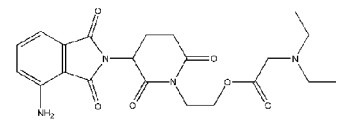
4-amino-2-(1-(2-hydroxyethyl)-2,6-dioxopiperidin-3-yl)isoindolin-1,3-dione 2-(diethylamino)acetate

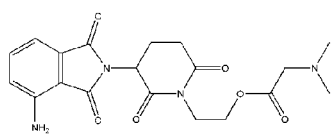
4-amino-2-(1-(2-hydroxyethyl)-2,6-dioxopiperidin-3-yl)isoindolin-1,3-dione 2-(dimethylamino)acetate

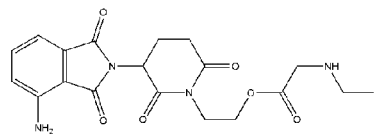
4-amino-2-(1-(2-hydroxyethyl)-2,6-dioxopiperidin-3-yl)isoindolin-1,3-dione 2-(ethylamino)acetate

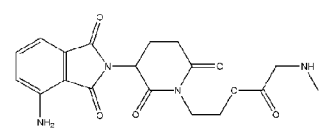
4-amino-2-(1-(2-hydroxyethyl)-2,6-dioxopiperidin-3-yl)isoindolin-1,3-dione 2-(methylamino)acetate

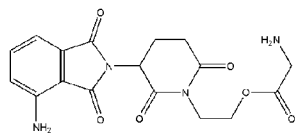
4-amino-2-(1-(2-hydroxyethyl)-2,6-dioxopiperidin-3-yl)isoindolin-1,3-dione 2-aminoacetate

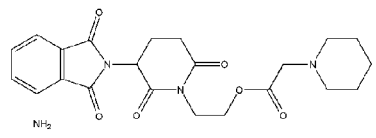
4-amino-2-(1-(2-hydroxyethyl)-2,6-dioxopiperidin-3-yl)isoindolin-1,3-dione 2-(1-piperidyl)acetate

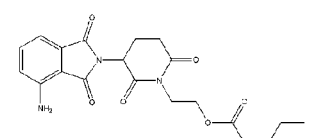
4-amino-2-(1-(2-hydroxyethyl)-2,6-dioxopiperidin-3-yl)isoindolin-1,3-dione (S)-2-(diethylamino)propanoate

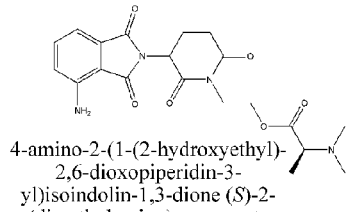
4-amino-2-(1-(2-hydroxyethyl)-2,6-dioxopiperidin-3-yl)isoindolin-1,3-dione (S)-2-(dimethylamino)propanoate

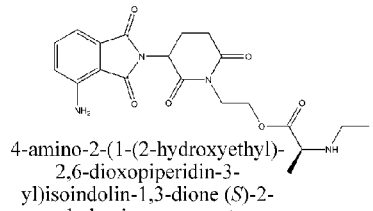
4-amino-2-(1-(2-hydroxyethyl)-2,6-dioxopiperidin-3-yl)isoindolin-1,3-dione (S)-2-ethylaminopropanoate

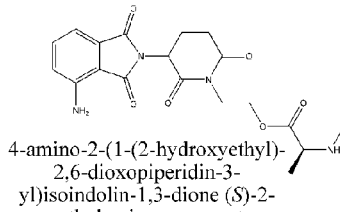
4-amino-2-(1-(2-hydroxyethyl)-2,6-dioxopiperidin-3-yl)isoindolin-1,3-dione (S)-2-methylaminopropanoate

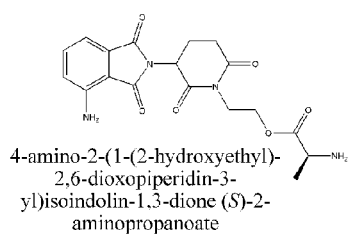
4-amino-2-(1-(2-hydroxyethyl)-2,6-dioxopiperidin-3-yl)isoindolin-1,3-dione (S)-2-aminopropanoate

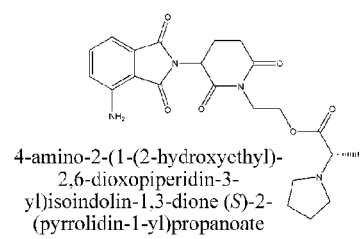
4-amino-2-(1-(2-hydroxyethyl)-2,6-dioxopiperidin-3-yl)isoindolin-1,3-dione (S)-2-(pyrrolidin-1-yl)propanoate

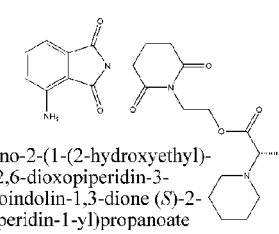
4-amino-2-(1-(2-hydroxyethyl)-2,6-dioxopiperidin-3-yl)isoindolin-1,3-dione (S)-2-(piperidin-1-yl)propanoate

Fig. 3

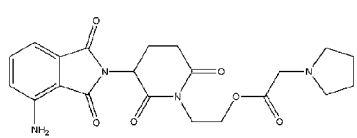

4-amino-2-(1-(2-hydroxyethyl)-
2,6-dioxopiperidin-3-
yl)isoindolin-1,3-dione 2-
(pyrrolidin-1-yl)acetate

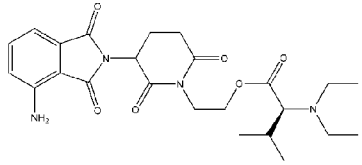

4-amino-2-(1-(2-hydroxyethyl)-
2,6-dioxopiperidin-3-
yl)isoindolin-1,3-dione (S)-2-
diethylamino-3-methylbutanoate

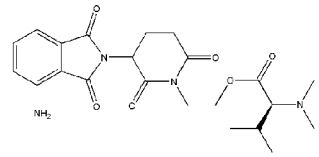

4-amino-2-(1-(2-hydroxyethyl)-
2,6-dioxopiperidin-3-yl)isoindolin-
1,3-dione (S)-2-dimethylamino-3-
methylbutanoate

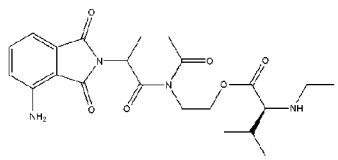

4-amino-2-(1-(2-hydroxyethyl)-
2,6-dioxopiperidin-3-
yl)isoindolin-1,3-dione (S)-2-
ethylamino-3-methylbutanoate

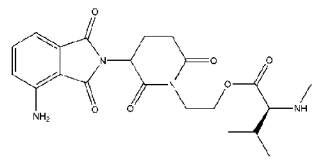

4-amino-2-(1-(2-hydroxyethyl)-
2,6-dioxopiperidin-3-
yl)isoindolin-1,3-dione (S)-2-
methylamino-3-methylbutanoate

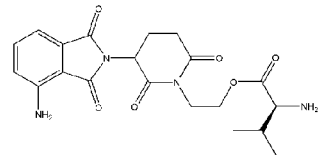

4-amino-2-(1-(2-hydroxyethyl)-
2,6-dioxopiperidin-3-
yl)isoindolin-1,3-dione (S)-2-
amino-3-methylbutanoate

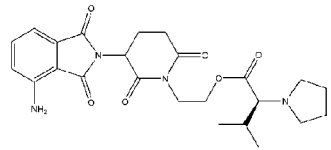

4-amino-2-(1-(2-hydroxyethyl)-
2,6-dioxopiperidin-3-
yl)isoindolin-1,3-dione (S)-2-
pyrrolidin-1-yl-3-methylbutanoate

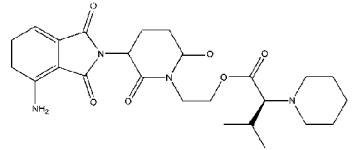

4-amino-2-(1-(2-hydroxyethyl)-
2,6-dioxopiperidin-3-
yl)isoindolin-1,3-dione (S)-2-
piperidin-1-yl-3-methylbutanoate

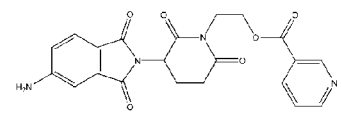

5-amino-2-(1-(2-hydroxyethyl)-
2,6-dioxopiperidin-3-
yl)isoindolin-1,3-dione nicotinate

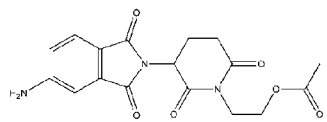

5-amino-2-(1-(2-hydroxyethyl)-
2,6-dioxopiperidin-3-
yl)isoindolin-1,3-dione acetate

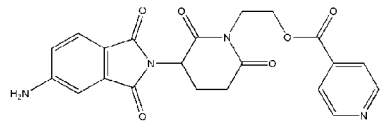

5-amino-2-(1-(2-hydroxyethyl)-2,6-
dioxopiperidin-3-yl)isoindolin-1,3-
dione isonicotinate

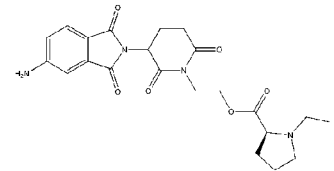

5-amino-2-(1-(2-hydroxyethyl)-2,6-
dioxopiperidin-3-yl)isoindolin-1,3-dione
N-ethyl-(S)-2-pyrrolidinecarboxylate

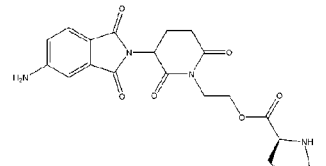

5-amino-2-(1-(2-hydroxyethyl)-2,6-
dioxopiperidin-3-yl)isoindolin-1,3-dione
(S)-2-pyrrolidinecarboxylate

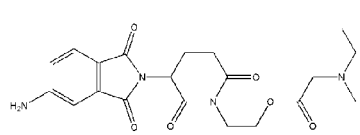

5-amino-2-(1-(2-hydroxyethyl)-2,6-
dioxopiperidin-3-yl)isoindolin-1,3-
dione 2-(diethylamino)acetate

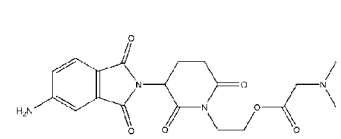

5-amino-2-(1-(2-hydroxyethyl)-2,6-
dioxopiperidin-3-yl)isoindolin-1,3-
dione 2-(dimethylamino)acetate

Fig. 4

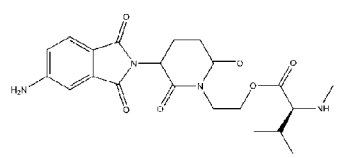

5-amino-2-(1-(2-hydroxyethyl)-2,6-dioxopiperidin-3-yl)isoindolin-1,3-dione (S)-2-methylamino-3-methylbutanoate

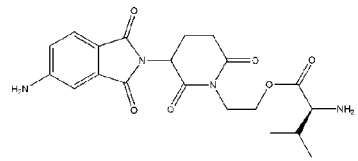

5-amino-2-(1-(2-hydroxyethyl)-2,6-dioxopiperidin-3-yl)isoindolin-1,3-dione (S)-2-amino-3-methylbutanoate

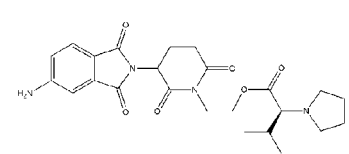

5-amino-2-(1-(2-hydroxyethyl)-2,6-dioxopiperidin-3-yl)isoindolin-1,3-dione (S)-2-pyrrolidin-1-yl-3-methylbutanoate

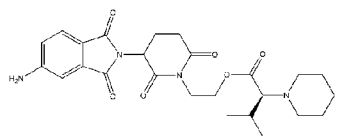

5-amino-2-(1-(2-hydroxyethyl)-2,6-dioxopiperidin-3-yl)isoindolin-1,3-dione (S)-2-piperidin-1-yl-3-methylbutanoate

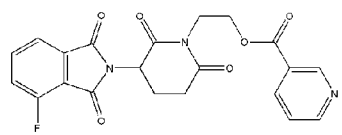

4-fluoro-2-(1-(2-hydroxyethyl)-2,6-dioxopiperidin-3-yl)isoindolin-1,3-dione nicotinate

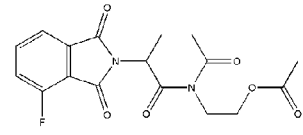

4-fluoro-2-(1-(2-hydroxyethyl)-2,6-dioxopiperidin-3-yl)isoindolin-1,3-dione acetate

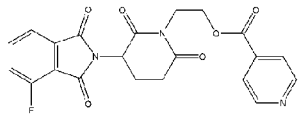

4-fluoro-2-(1-(2-hydroxyethyl)-2,6-dioxopiperidin-3-yl)isoindolin-1,3-dione isonicotinate

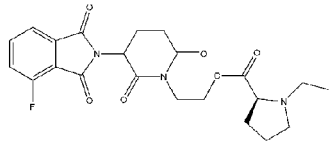

4-fluoro-2-(1-(2-hydroxyethyl)-2,6-dioxopiperidin-3-yl)isoindolin-1,3-dione N-ethyl-(S)-2-pyrrolidinecarboxylate

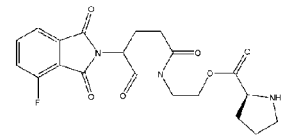

4-fluoro-2-(1-(2-hydroxyethyl)-2,6-dioxopiperidin-3-yl)isoindolin-1,3-dione (S)-2-pyrrolidinecarboxylate

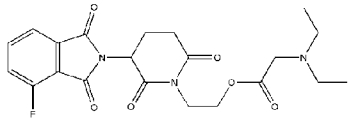

4-fluoro-2-(1-(2-hydroxyethyl)-2,6-dioxopiperidin-3-yl)isoindolin-1,3-dione 2-(diethylamino)acetate

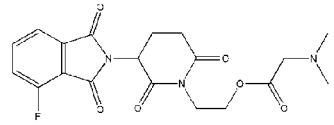

4-fluoro-2-(1-(2-hydroxyethyl)-2,6-dioxopiperidin-3-yl)isoindolin-1,3-dione 2-(dimethylamino)acetate

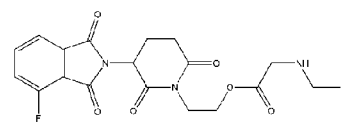

4-fluoro-2-(1-(2-hydroxyethyl)-2,6-dioxopiperidin-3-yl)isoindolin-1,3-dione 2-(ethylamino)acetate

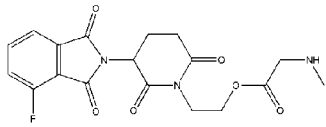

4-fluoro-2-(1-(2-hydroxyethyl)-2,6-dioxopiperidin-3-yl)isoindolin-1,3-dione 2-(methylamino)acetate

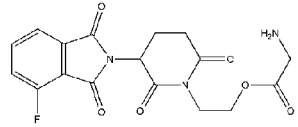

4-fluoro-2-(1-(2-hydroxyethyl)-2,6-dioxopiperidin-3-yl)isoindolin-1,3-dione 2-aminoacetate

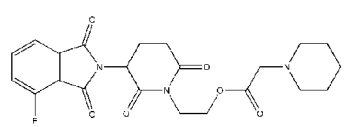

4-fluoro-2-(1-(2-hydroxyethyl)-2,6-dioxopiperidin-3-yl)isoindolin-1,3-dione 2-(1-piperidyl)acetate

Fig. 6

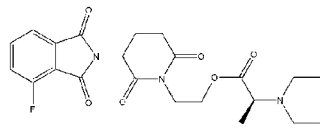
4-fluoro-2-(1-(2-hydroxyethyl)-
2,6-dioxopiperidin-3-
yl)isoindolin-1,3-dione (S)-2-
(diethylamino)propanoate

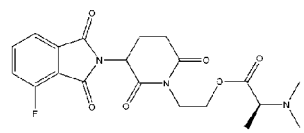
4-fluoro-2-(1-(2-hydroxyethyl)-
2,6-dioxopiperidin-3-
yl)isoindolin-1,3-dione (S)-2-
(dimethylamino)propanoate

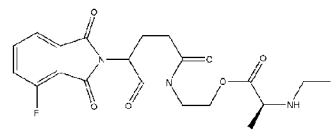
4-fluoro-2-(1-(2-hydroxyethyl)-
2,6-dioxopiperidin-3-
yl)isoindolin-1,3-dione (S)-2-
ethylaminopropanoate

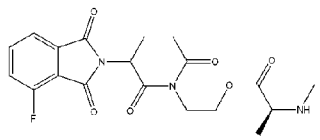
4-fluoro-2-(1-(2-hydroxyethyl)-
2,6-dioxopiperidin-3-
yl)isoindolin-1,3-dione (S)-2-
methylaminopropanoate

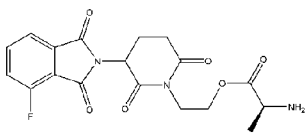
4-fluoro-2-(1-(2-hydroxyethyl)-
2,6-dioxopiperidin-3-
yl)isoindolin-1,3-dione (S)-2-
aminopropanoate

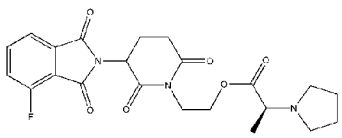
4-fluoro-2-(1-(2-hydroxyethyl)-
2,6-dioxopiperidin-3-
yl)isoindolin-1,3-dione (S)-2-
(pyrrolidin-1-yl)propanoate

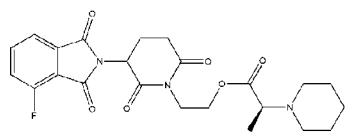
4-fluoro-2-(1-(2-hydroxyethyl)-
2,6-dioxopiperidin-3-
yl)isoindolin-1,3-dione (S)-2-
(piperidin-1-yl)propanoate

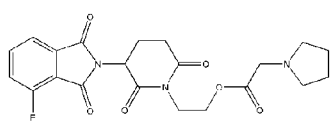
4-fluoro-2-(1-(2-hydroxyethyl)-
2,6-dioxopiperidin-3-
yl)isoindolin-1,3-dione 2-
(pyrrolidin-1-yl)acetate

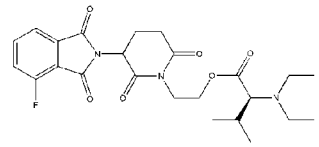
4-fluoro-2-(1-(2-hydroxyethyl)-
2,6-dioxopiperidin-3-
yl)isoindolin-1,3-dione (S)-2-
diethylamino-3-methylbutanoate

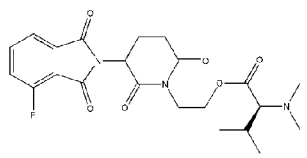
4-fluoro-2-(1-(2-hydroxyethyl)-
2,6-dioxopiperidin-3-yl)isoindolin-
1,3-dione (S)-2-dimethylamino-3-
methylbutanoate

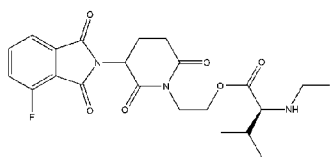
4-fluoro-2-(1-(2-hydroxyethyl)-
2,6-dioxopiperidin-3-
yl)isoindolin-1,3-dione (S)-2-
ethylamino-3-methylbutanoate

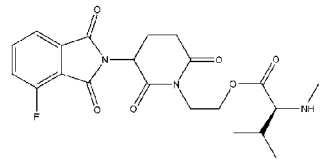
4-fluoro-2-(1-(2-hydroxyethyl)-
2,6-dioxopiperidin-3-
yl)isoindolin-1,3-dione (S)-2-
methylamino-3-methylbutanoate

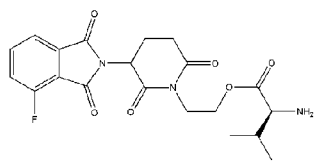
4-fluoro-2-(1-(2-hydroxyethyl)-
2,6-dioxopiperidin-3-
yl)isoindolin-1,3-dione (S)-2-
amino-3-methylbutanoate

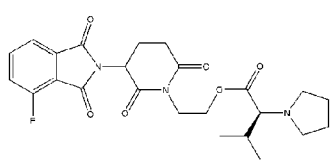
4-fluoro-2-(1-(2-hydroxyethyl)-
2,6-dioxopiperidin-3-
yl)isoindolin-1,3-dione (S)-2-
pyrrolidin-1-yl-3-methylbutanoate

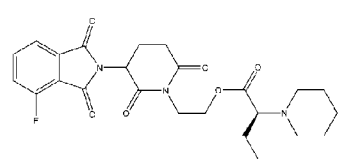
4-fluoro-2-(1-(2-hydroxyethyl)-
2,6-dioxopiperidin-3-
yl)isoindolin-1,3-dione (S)-2-
piperidin-1-yl-3-methylbutanoate

Fig. 7

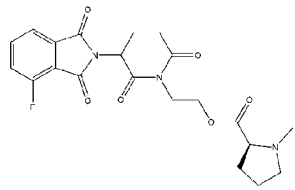

4-fluoro-2-(1-(2-hydroxyethyl)-2,6-dioxopiperidin-3-yl)isoindolin-1,3-dione N-methyl-(S)-2-pyrrolidinecarboxylate

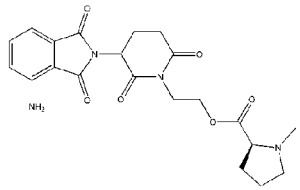

4-amino-2-(1-(2-hydroxyethyl)-2,6-dioxopiperidin-3-yl)isoindolin-1,3-dione N-methyl-(S)-2-pyrrolidinecarboxylate

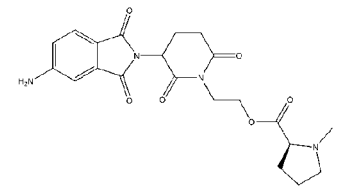

5-amino-2-(1-(2-hydroxyethyl)-2,6-dioxopiperidin-3-yl)isoindolin-1,3-dione N-methyl-(S)-2-pyrrolidinecarboxylate

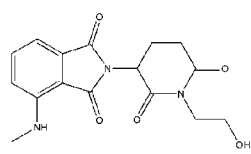

2-(1-(2-hydroxyethyl)-2,6-dioxopiperidin-3-yl)-4-(methylamino)isoindoline-1,3-dione

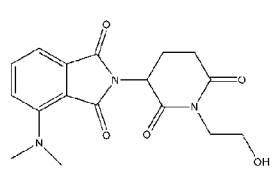

4-(dimethylamino)-2-(1-(2-hydroxyethyl)-2,6-dioxopiperidin-3-yl)isoindoline-1,3-dione

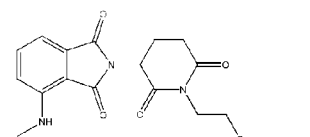

4-(methylamino)-2-(2,6-dioxo-1-(2-propoxyethyl)piperidin-3-yl)isoindoline-1,3-dione

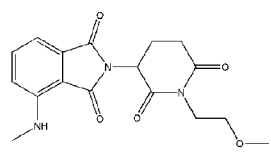

2-(1-(2-methoxyethyl)-2,6-dioxopiperidin-3-yl)-4-(methylamino)isoindoline-1,3-dione

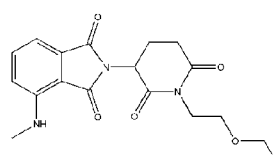

2-(1-(2-ethoxyethyl)-2,6-dioxopiperidin-3-yl)-4-(methylamino)isoindoline-1,3-dione

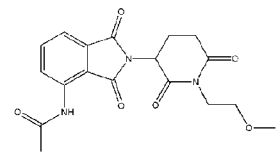

N-(2-(1-(2-methoxyethyl)-2,6-dioxopiperidin-3-yl)-1,3-dioxoisoindolin-7-yl)acetamide

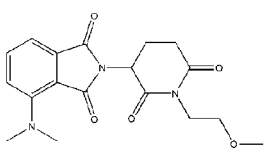

4-(dimethylamino)-2-(1-(2-methoxyethyl)-2,6-dioxopiperidin-3-yl)isoindoline-1,3-dione

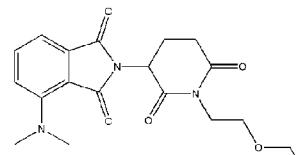

4-(dimethylamino)-2-(1-(2-ethoxyethyl)-2,6-dioxopiperidin-3-yl)isoindoline-1,3-dione

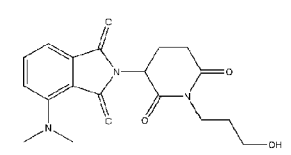

4-(dimethylamino)-2-(1-(3-hydroxypropyl)-2,6-dioxopiperidin-3-yl)isoindoline-1,3-dione

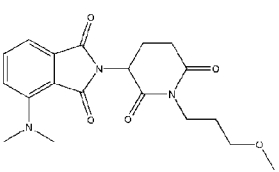

4-(dimethylamino)-2-(1-(3-methoxypropyl)-2,6-dioxopiperidin-3-yl)isoindoline-1,3-dione

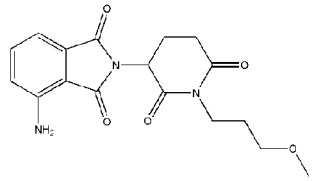

4-amino-2-(1-(3-methoxypropyl)-2,6-dioxopiperidin-3-yl)isoindoline-1,3-dione

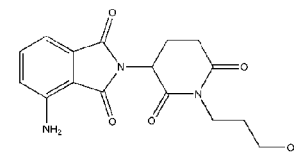

4-amino-2-(1-(3-hydroxypropyl)-2,6-dioxopiperidin-3-yl)isoindoline-1,3-dione

Fig. 8

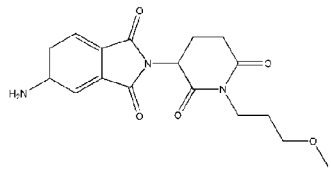
5-amino-2-(1-(3-methoxypropyl)-2,6-dioxopiperidin-3-yl)isoindoline-1,3-dione

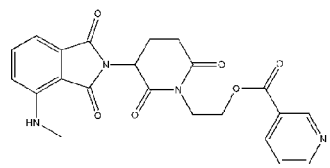
4-(methylamino)-2-(1-(2-hydroxyethyl)-2,6-dioxopiperidin-3-yl)isoindolin-1,3-dione nicotinate

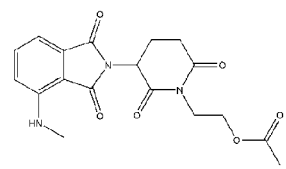
4-(methylamino)-2-(1-(2-hydroxyethyl)-2,6-dioxopiperidin-3-yl)isoindolin-1,3-dione acetate

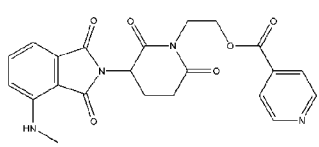
4-(methylamino)-2-(1-(2-hydroxyethyl)-2,6-dioxopiperidin-3-yl)isoindolin-1,3-dione isonicotinate

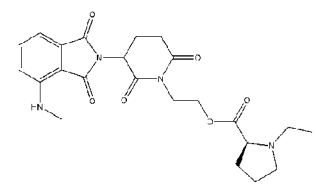
4-(methylamino)-2-(1-(2-hydroxyethyl)-2,6-dioxopiperidin-3-yl)isoindolin-1,3-dione N-ethyl-(S)-2-pyrrolidinecarboxylate

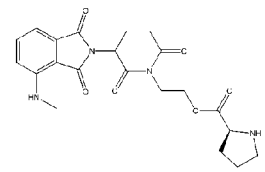
4-(methylamino)-2-(1-(2-hydroxyethyl)-2,6-dioxopiperidin-3-yl)isoindolin-1,3-dione (S)-2-pyrrolidinecarboxylate

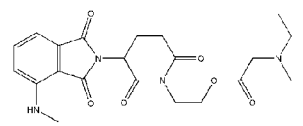
4-(methylamino-)2-(1-(2-hydroxyethyl)-2,6-dioxopiperidin-3-yl)isoindolin-1,3-dione 2-(diethylamino)acetate

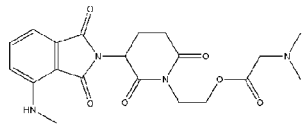
4-(methylamino)-2-(1-(2-hydroxyethyl)-2,6-dioxopiperidin-3-yl)isoindolin-1,3-dione 2-(dimethylamino)acetate

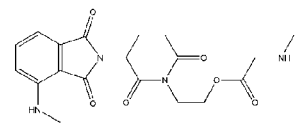
4-(methylamino-)2-(1-(2-hydroxyethyl)-2,6-dioxopiperidin-3-yl)isoindolin-1,3-dione 2-(ethylamino)acetate

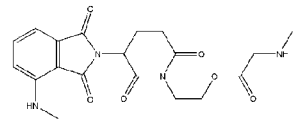
4-(methylamino-)2-(1-(2-hydroxyethyl)-2,6-dioxopiperidin-3-yl)isoindolin-1,3-dione 2-(methylamino)acetate

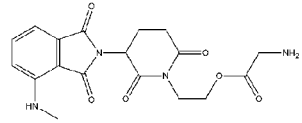
4-(methylamino)-2-(1-(2-hydroxyethyl)-2,6-dioxopiperidin-3-yl)isoindolin-1,3-dione 2-aminoacetate

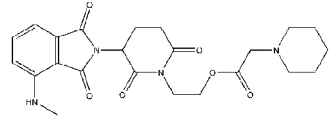
4-(methylamino)-2-(1-(2-hydroxyethyl)-2,6-dioxopiperidin-3-yl)isoindolin-1,3-dione 2-(1-piperidyl)acetate

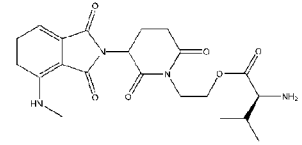
4-(methylamino)-2-(1-(2-hydroxyethyl)-2,6-dioxopiperidin-3-yl)isoindolin-1,3-dione (S)-2-amino-3-methylbutanoate

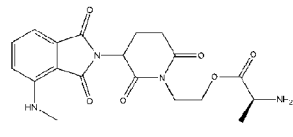
4-(methylamino)-2-(1-(2-hydroxyethyl)-2,6-dioxopiperidin-3-yl)isoindolin-1,3-dione (S)-2-aminopropanoate

Fig. 9

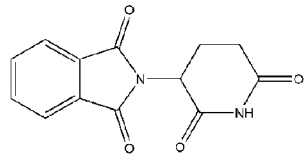

2-(2,6-dioxopiperidin-3-yl)isoindoline-1,3-dione

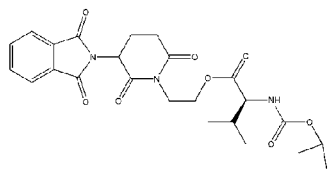

2-(1-(2-hydroxyethyl)-2,6-dioxopiperidin-3-yl)isoindolin-1,3-dione (S)-2-(tert-butoxycarbonylamino)-3-methylbutanoate

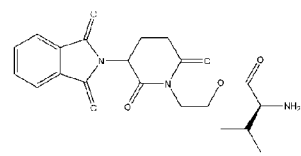

2-(1-(2-hydroxyethyl)-2,6-dioxopiperidin-3-yl)isoindoline-1,3-dione (S)-2-amino-3-methylbutanoate

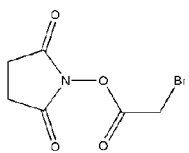

2,5-dioxopyrrolidinyl bromoacetate

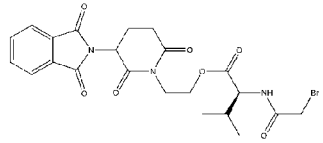

2-(1-(2-hydroxyethyl)-2,6-dioxopiperidin-3-yl)isoindolin-1,3-dione (S)-2-(2-bromoacetamido)-3-methylbutanoate

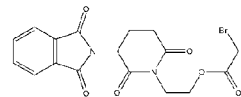

2-(1-(2-hydroxyethyl)-2,6-dioxopiperidin-3-yl)isoindolin-1,3-dione bromoacetate

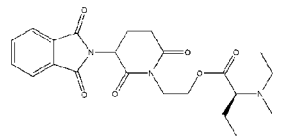

2-(1-(2-hydroxyethyl)-2,6-dioxopiperidin-3-yl)isoindolin-1,3-dione (S)-2-(diethylamino)-3-methylbutanoate

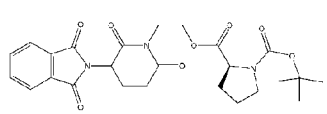

2-(1-(2-hydroxyethyl)-2,6-dioxopiperidin-3-yl)isoindolin-1,3-dione N-tert-butoxycarbonyl-(S)-2-pyrrolidinecarboxylate

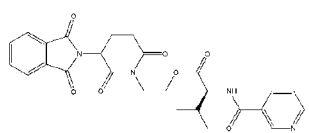

2-(1-(2-hydroxyethyl)-2,6-dioxopiperidin-3-yl)isoindolin-1,3-dione (S)-2-(nicotinamido)-3-methylbutanoate

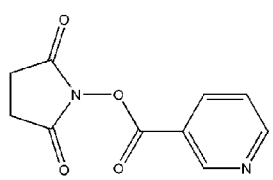

2,5-dioxopyrrolidinyl nicotinate

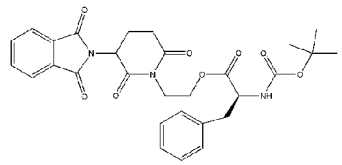

2-(1-(2-hydroxyethyl)-2,6-dioxopiperidin-3-yl)isoindolin-1,3-dione (S)-2-(tert-butoxycarbonylamino)-3-phenylpropanoate

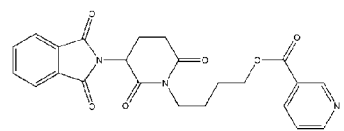

2-(1-(4-hydroxybutyl)-2,6-dioxopiperidin-3-yl)isoindolin-1,3-dione nicotinate

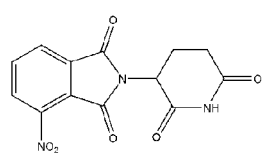

4-nitro-2-(2,6-dioxopiperidin-3-yl)isoindoline-1,3-dione

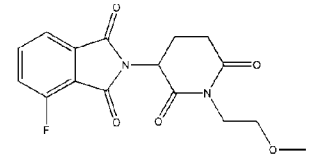

4-fluoro-2-(1-(2-methoxyethyl)-2,6-dioxopiperidin-3-yl)-4-nitroisoindoline-1,3-dione

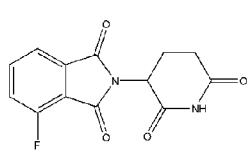

4-fluoro-2-(2,6-dioxopiperidin-3-yl)isoindoline-1,3-dione

Fig. 10

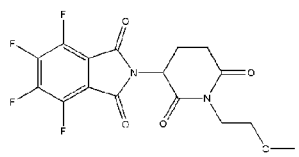
4,5,6,7-tetrafluoro-2-(1-(2-methoxyethyl)-2,6-dioxopiperidin-3-yl)-4-nitroisoindoline-1,3-dione
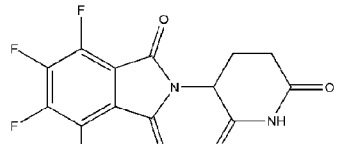
4,5,6,7-tetrafluoro-2-(2,6-dioxopiperidin-3-yl)isoindoline-1,3-dione
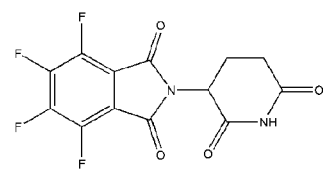
4,5,6,7-tetrafluoro-2-(2,6-dioxopiperidin-3-yl)isoindoline-1,3-dione
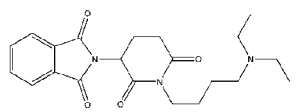
2-(1-(4-(diethylamino)butyl)-2,6-dioxopiperidin-3-yl)isoindoline-1,3-dione
Fig. 11

PIPERIDINE-2, 6-DIONE DERIVATIVES AND THEIR USE AS TUMOR NECROSIS FACTOR INHIBITORS

CROSS-REFERENCE TO RELATED APPLICATIONS

This application is a continuation of International Patent Application No. PCT/CN2005/001467 with an international filing date of Sep. 13, 2005, designating the United States, now pending, and further claims priority benefits to Chinese Patent Application No 200510013292.3, filed Apr. 7, 2005. The contents of the aforementioned specifications are incorporated herein by reference.

BACKGROUND OF THE INVENTION

1. Field of the Invention

This invention concerns piperidine-2,6-dione derivatives which are active as inhibitors of tumor necrosis factor released by cells, the preparation of these derivatives, as well as their application as pharmaceutically-active ingredients.

2. Description of the Related Art

Tumor necrosis factor α (TNFα) is a cytokine, mainly produced by macrophages, which causes inflammation, fever, cardiovascular dysfunction, hemorrhage and a series of acute reactions similar to acute infection and shock when it is applied in humans and animals. Excessive or uncontrolled TNFα in animals or humans often indicates one of the following diseases:

1) Endotoxaemia and/or toxic shock syndrome [Tracey et al., Nature 330, 662-4 1987; Hinshaw et al., Circ Shock 30, 279-92 (1990)];
2) Cachexia [Dezube et al., Laucet, 335(8690), 662 (1990)]; or
3) Adult Respiratory Distress Syndrome (ARDS) [Millar et al., Laucet 2(8665), 712-714 (1989)].

TNFα also plays an important role in bone resorption diseases including arthritis [Betolinni et al., Nature 319, 516-8 (1986)]. TNFα may stimulate bone resorption by stimulating the formation and activation of osteoclast and resist the formation of bone, which was shown both by in vitro and in vivo experiments.

At the present, a disease which is most commonly linked to TNFα released by tumor and host tissue is hypercalcemia, which is closely related to malignant tumors [Calci. Tissue Int. (US) 46(Suppl.), S3-10 (1990)]. The immune response is closely related to an increased concentration of TNFα in serum of the patient after bone marrow transplantation [Holler et al., Blood, 75(4), 1011-1016 (1990)].

Fatal hyperacute neurogenic syndrome brainstem-type malaria, which is the most dangerous type of malaria, is also linked to high levels of TNFα in blood. When this kind of malaria occurs, the levels of TNFα in serum is directly related to the disease, which often occurs during an acute attack of malaria in patients [Grau et al., N. Engl. J. Med. 320(24), 1586-91 (1989)].

TNFα plays an important role in chronic pneumonia as well. The storage of silicon-containing particles can cause silicosis. Silicosis is a pulmonary fibrosis, which causes progressive respiratory failure. In an animal pathological model, TNFα antibody can fully block the progress of mice lung fibrosis caused by silica dust [Pignet et al., Nature, 344:245-7 (1990)]. It was also proved that TNFα levels are abnormally high in serum of animals with pulmonary fibrosis caused by silica dust or asbestos dust in animal experiments [Bissonnette et al., Inflammation 13(3), 329-339 (1989)]. Pathological research reveals that TNFα levels in the lungs of Pneumal Sarcoidosis patients is much higher than that of ordinary people [Baughman et al., J. Lab. Clin. Med. 115(1), 36-42 (1990)]. It follows that TNFα inhibitor should have a great significance in the treatment of chronic pulmonary disease and lung injury.

The reason for inflammation occurring in the body of patient having reperfusion injury may be abnormal levels of TNFα. TNFα is regarded as the chief cause inducing tissue injury caused by ischemia [Uadder et al., PNAS 87, 2643-6 (1990)].

Besides, it has been shown that TNFα may start retroviral replication including that of HIV-1 [Duh et al., Proc. Nat. Acad. Sci., 86, 5974-8 (1989)]. T-cells need to be activated before HIV infects them. Once the activated T-cells are infected by virus (HIV), those T-cells must be in an activated state so that HIV virus genes are able to be expressed and/or replicated successfully. Cytokines, especially TNFα, play an important role in the process of HIV protein expression or viral replication controlled by T-cells. So, inhibition of TNFα formation can in turn inhibit HIV replication in T-cells [Poll et al., Proc. Nat. Acad. Sci., 87, 782-5 (1990); Monto et al., Blood 79, 2670 (1990); Poll et al., AIDS Res. Human Retrovirus, 191-197 (1992)].

cAMP can control many functions of cells, such as inflammation response, including asthma, and inflammation [Lome and Cheng, Drugs of the futune, 17(9), 799-807, 1992]. When inflammation occurs, increased cAMP concentration in white cells inhibits white cell activation and then releases inflammation regulatory factors including TNFα so as to exacerbate inflammation in patients. Consequently, the inhibition of TNFα release can alleviate inflammation diseases including asthma.

Several doctors, including Yu Yanyan, have found that TNFα plays an important role in the process of liver necrosis in viral hepatitis patients. [Yu Yanyan etc., Chinese Journal of Internal Medicine 1996, 35:28-31]. This shows that TNFα inhibitors may play a great role in the treatment of chronic hepatic disease and liver injury.

Several researchers, including Li Yingxu, have found that levels of tumor necrosis factors are significantly increased on synthesis and secretion of human monocyte in patients with chronic hepatic disease and other cell factor secretions are induced (for example, II-1β, II-6 and II-8). They are both involved in hepatocellular injury process [Journal of Qiqihar Medical Colleg, 22(10):1119-1120, 2001]. Their results are in accordance with the conclusions of Yoshioka etc. [Hepatology, 1989, 10:769-777] and Wang Xin etc. [Chinese Journal of Infectious Diseases, 1997, 15(2):85-88]. It has also been found that thalidomide, the small molecular inhibitor of TNFα, is able to inhibit TNFα secreted by human monocyte in hepatitis patients, which lays a foundation of molecular pathology for TNFα inhibitor applied on hepatitis, cirrhosis and liver cancer therapy.

TNFα induces certain inflammation responses, such as aggregation and adhesion of inflammatory cells, increased dilatation and permeability of micro-vessels, fever, increased neutrophil in circulation, and hemodynamic changes, and further causes kidney cell injury by stimulating synthesis and release of inflammation cytokine [Abboud H. E. Kidney Int. 1993; 43:252-267], expression of cell adhesion molecule [Egido J. et al., Kidney Int. 1993; 43(suppl 39):59-64], synthesis and release of prostaglandin $G_2$ ($PGE_2$) and platelet-activating factor (PAF)[Gammusi G. et al., Kidney Int., 43(suppl 39):32-36]. It has been shown that TNFα plays an important role in the development of nephritis.

TNFα regulates the differentiation of B lymphocytes and reinforces the cytotoxicity of natural killer cells (NK), so as to participate in the regulation of immunological function by the activation of hyperplasia of macrophages and immunologically stimulating T-lymphocytes.

Therefore, it is an effective strategy to decrease TNFα levels and/or increase cAMP levels so as to cure many inflammatory, infectious, immunological or malignant tumor diseases, including but not limited to septic shock, endotoxic shock, hemodynamic shock, septic syndrom, post ischemic reperfusion injury, malaria, mycobacterial infection, meningitis, psoriasis, congestive heart failure, fibrotic disease, cachexia, transplant immune rejection, cancer, autoimmune disease, opportunistic infection in AIDS, rheumatoid arthritis (RA), hepatitis, nephritis, rheumatoid spondylitis, and so on. Accordingly, research and development on small molecular TNFα inhibitors with low toxicity and high efficiency has a great public significance and economic value.

SUMMARY OF THE INVENTION

In one aspect, this invention is directed to derivatives of piperidine-2,6-dione, their organic or inorganic salts thereof, methods to synthesize these derivatives, and their application as pharmaceutically-active ingredients as inhibitors of TNFα releasing in cells, the derivatives of piperidine-2,6-dione being of the general formula (I):

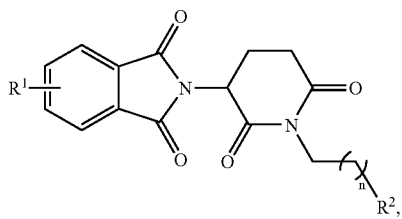

wherein n represents 1, 2, 3, 4, 5 or 6; $R^1$ represents from one to four of the same or different substituents selected from F, Cl, Br, $C_{1-4}$ alkyl, OH, $OC_{1-4}$ alkyl, $NO_2$, $NHC(O)C_{1-4}$ alkyl, $NH_2$, $NH(C_{1-4}$ alkyl), $N(C_{1-4}$ alkyl)$_2$; $R^2$ represents $OR^3$, $NR^3R^4$, $N(R^3)COR^4$, $O_2CR^5$; $R^3$ and $R^4$ represent independently and at each occurrence H or $C_{1-4}$ alkyl; $R^5$ represents $CHR^6NR^7R^8$, $CHR^6NR^9C(O)CHR^{10}NR^7R^8$, a heterocycle W or $CHR^6NR^9C(O)W$; $R^6$, $R^9$, $R^{10}$ represent independently and at each occurrence H, or $C_{1-4}$ alkyl; $R^7$ and $R^8$ represent independently and at each occurrence H, $C_{1-4}$ alkyl, or $R^7$ and $R^8$ taken together represent 1,3-propylene, 1,4-butylene, 1,5-pentylene, or 1,6-hexylene; W represents a four-membered, a five-membered, a six-membered, a seven-membered, or an eight-membered saturated or unsaturated heterocycle.

When W represents a heterocycle, it includes a four-membered, a five-membered, a six-membered, a seven-membered or an eight-membered saturated, or unsaturated heterocycle or aromatic heterocycle, bearing one or multiple heteroatoms such as nitrogen atom, oxygen atom or sulfur atom, and particularly, 2-pyridyl, 3-pyridyl, 4-pyridyl, 2-pyrimidinyl, 3-pyrimidinyl, 4-pyrimidinyl, or heterocycles of formula (II), (III), (IV), or (V), in which X represents O, S, or $NR^{12}$; Y represents 1,2-ethylene, 1,3-propylene, 1,4-butylene, 1,5-pentylene, 1,6-hexylene, —$CH_2OCH_2$—, —$CH_2SCH_2$— or —$CH_2NR^{12}CH_2$—; and $R^{11}$ and $R^{12}$ represent independently and at each occurrence H, or $C_{1-4}$alkyl. $R^3$, $R^4$, $R^6$, $R^9$, $R^{10}$, $R^{11}$, or $R^{12}$ may be substituted by substituents

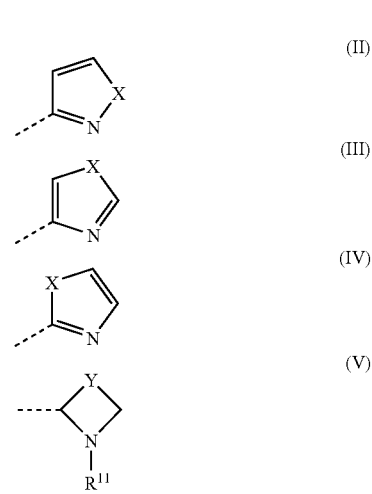

such as OH, COOH, $C(O)NH_2$, $NHC(O)R^{13}$, $NH_2$, $NHR^{14}$, $NR^{15}R^{16}$, $NHC(O)NH_2$, $NHC(NH)NH_2$, $OR^{17}$, $SR^{18}$, phenyl or substituted phenyl, etc, when $R^3$, $R^4$, $R^6$, $R^9$, $R^{10}$, $R^{11}$, $R^{12}$ represent $C_{1-4}$ alkyl, including straight chain or branched chain alkyl, wherein $R^{13}R^{14}$, $R^{15}$, $R^{16}$, $R^{17}$ and $R^{18}$ represent independently and at each occurrence H, or $C_{1-4}$ alkyl.

$R^7$ and $R^8$ may be substituted by substituents such as OH, COOH, $C(O)NH_2$, $NHC(O)R^{13}$, $NH_2$, $NHR^{14}$, $NR^{15}R^{16}$, $NHC(O)NH_2$, $NHC(NH)NH_2$, $OR^{17}$, $SR^{18}$, phenyl, or substituted phenyl, etc, when $R^7$ and $R^8$ independently represent $C_{1-4}$ alkyl, including straight chain or branched chain alkyl, wherein $R^{13}$, $R^{14}$, $R^{15}$, $R^{16}$, $R^{17}$, and $R^{18}$ represent independently and at each occurrence H, or $C_{1-4}$ alkyl.

$R^7$ and $R^8$ may be substituted by substituents such as OH, COOH, $C(O)NH_2$, $NHC(O)R^{13}$, $NH_2$, $NHR^{14}$, $NR^{15}R^{16}$, $NHC(O)NH_2$, $NHC(NH)NH_2$, $OR^{17}$, $SR^{18}$, phenyl or substituted phenyl, etc., when $R^7$ and $R^8$ taken together represent 1,3-propylene, 1,4-butylene, 1,5-pentylene, or 1,6-hexylene, wherein $R^{13}$, $R^{14}$, $R^{15}$, $R^{16}$, $R^{17}$, and $R^{18}$ represent independently and at each occurrence H, or $C_{1-4}$ alkyl.

When W represents a heterocycle, it includes four-membered, five-membered, six-membered, seven-membered or eight-membered saturated, or unsaturated heterocycles or aromatic heterocycles including one or multiple heteroatoms, such as nitrogen atom, oxygen atom or sulfur atom, which can be substituted by OH, COOH, $C(O)NH_2$, $NHC(O)R^{13}$, $NH_2$, $NHR^{14}$, $NR^{15}R^{16}$, $NHC(O)NH_2$, $NHC(NH)NH_2$, $OR^{17}$, $SR^{18}$ $OR^{19}$, wherein $R^{13}$, $R^{14}$, $R^{15}$, $R^{16}$, $R^{17}$, $R^{18}$, $R^{19}$ represent independently and at each occurrence H, or $C_{1-4}$ alkyl.

The compounds of formula (I) appropriate for medical use include those compounds wherein n represents an integer from one to six, and particularly those compounds, wherein n represents one, two or three.

The compounds of formula (I) appropriate for medical use include those compounds wherein $R^1$ represents from one to four of same or different substituents selected from: H, F, Cl, Br, $CH_3$, $CH_2CH_3$, OH, $OCH_3$, $OCH_2CH_3$, $NH_2$, $NHCH_3$, $NHCH_2CH_3$, $N(CH_3)_2$; and particularly the compounds wherein $R^1$ represents H, 3-F, 4-F, 3-$NH_2$, 4-$NH_2$, or 3,4,5,6-tetrafluoro.

The compounds of formula (I) appropriate for medical use include those compounds wherein $R^5$ represents $CHR^6NR^8R^7$; $R^6$ represents H, $CH_3$, $CH_2CH_3$, $CH_2CH_2CH_3$, $CH(CH_3)_2$, $CH_2CH_2CH_2CH_3$, $CH_2CH(CH_3)_2$, or $CH(CH_3)$ $CH_2CH_3$; $R^7$ and $R^8$ represent independently and at each occurrence H, $CH_3$, $CH_2CH_3$, $CH_2CH_2CH_3$, $CH(CH_3)_2$, $CH_2CH_2CH_2CH_3$, $CH_2CH(CH_3)_2$, or $CH(CH_3)CH_2CH_3$; $R^7$ and $R^8$ taken together represent 1,4-butylene, 1,5-pentylene; and particularly those compounds wherein $R^6$ represents H, $CH_3$, or $CH(CH_3)_2$; $R^7$ and $R^8$ represent independently and at each occurrence H, $CH_3$, $CH_2CH_3$; or $R^7$ and $R^8$ taken together represent 1,4-butylene, or 1,5-pentylene.

When $R^5$ represents $CHR^6NR^9C(O)CHR^{10}NR^7R^8$, the compounds of formula (I) appropriate for medical use include those in which $R^6$ and $R^{10}$ independently and at each occurrence represent H, $CH_3$, $CH(CH_3)_2$, $CH_2CH(CH_3)_2$, or $CH(CH_3)CH_2CH_3$; $R^9$ represents H, $CH_3$, $CH_2CH_3$, $CH_2CH_2CH_3$, $CH(CH_3)_2$, $R^8$ and $R^7$ each independently and at each occurrence represent H, $CH_3$, $CH_2CH_3$, $CH_2CH_2CH_3$, $CH(CH_3)_2$, or $R^8$ and $R^7$ taken together represent 1,4-butylene, or 1,5-pentylene; and particularly compounds of formula (I) appropriate for medical use include those derivatives of piperidine-2,6-dione in which $R^6$ and $R^{10}$ independently and at each occurrence represent H, $CH_3$ or $CH(CH_3)_2$, $R^9$ represents H, $CH_3$, $CH_2CH_3$; and $R^8$ and $R^7$ independently and at each occurrence represent H, $CH_3$, $CH_2CH_3$ or $R^8$ and $R^7$ taken together represent 1,4-butylene or 1,5-pentylene.

The compounds of formula (I) appropriate for medical use include those compounds wherein $R^5$ represents W, and W represents 2-pyridyl, 3-pyridyl, 4-pyridyl, 2-pyrimidinyl, 4-pyrimidinyl, 5-pyrimidinyl, 2-pyrrolidinyl, 2-(N-methyl)pyrrolidinyl, 2-(N-ethyl)pyrrolidinyl, 2-(N-propyl)pyrrolidinyl, or 2-(N-isopropyl)pyrrolidinyl. Among them, those particularly appropriate for medical use include those compounds in which W represents 3-pyridyl, 2-pyrrolidinyl, 2-(N-methyl)pyrrolidinyl, or 2-(N-ethyl)pyrrolidinyl.

The compounds of formula (I) appropriate for medical use include those derivatives of piperidine-2,6-dione wherein $R^5$ represents $CHR^6NR^9C(O)W$.

Among the compounds of formula (I) appropriate for medical use wherein $R^5$ represents $CHR^6NR^9C(O)W$ are included derivatives of piperidine-2,6-dione wherein $R^6$ and $R^9$ independently and at each occurrence represent H, $CH_3$, $CH_2CH_3$, $CH_2CH_2CH_3$ or $CH(CH_3)_2$, and W represents 2-pyridyl, 3-pyridyl, 4-pyridyl, 2-pyrimidinyl, 4-pyrimidinyl, 5-pyrimidinyl, 2-pyrrolidinyl, 2-(N-methyl)pyrrolidinyl, 2-(N-ethyl)pyrrolidinyl, 2-(N-propyl)pyrrolidinyl, or 2-(N-isopropyl)pyrrolidinyl. Those compounds particularly appropriate for medicinal purposes include compounds of formula (I) wherein $R^6$ represents H, $CH_3$ or $CH(CH_3)_2$, $R^9$ represents H, $CH_3$, $CH_2CH_3$; and W represents 3-pyridyl, 2-pyrrolidinyl, 4-pyridyl, 2-(N-methyl)-pyrrolidinyl, or 2-(N-ethyl)pyrrolidinyl.

Particular derivatives of piperidine-2,6-dione appropriate for medical use as active ingredient include but are not limited to the following compounds:

1) 4-amino-2-(1-(2-methoxyethyl)-2,6-dioxopiperidin-3-yl)isoindoline-1,3-dione;
2) 4-amino-2-(1-(2-hydroxyethyl)-2,6-dioxopiperidin-3-yl)isoindoline-1,3-dione;
3) 4-fluoro-2-(1-(2-hydroxyethyl)-2,6-dioxopiperidin-3-yl)isoindoline-1,3-dione;
4) 5-amino-2-(1-(2-hydroxyethyl)-2,6-dioxopiperidin-3-yl)isoindoline-1,3-dione;
5) 5-amino-2-(1-(2-methoxyethyl)-2,6-dioxopiperidin-3-yl)isoindoline-1,3-dione
6) 2-(1-(2-methoxyethyl)-2,6-dioxopiperidin-3-yl)-4-nitroisoindoline-1,3-dione;
7) 2-(1-(2-hydroxyethyl)-2,6-dioxopiperidin-3-yl)-4-nitroisoindoline-1,3-dione;
8) 2-(1-(2-hydroxyethyl)-2,6-dioxopiperidin-3-yl)isoindoline-1,3-dione;
9) 2-(1-(4-hydroxybutyl)-2,6-dioxopiperidin-3-yl)isoindoline-1,3-dione;
10) 2-(1-(2-hydroxyethyl)-2,6-dioxopiperidin-3-yl)isoindolin-1,3-dione 2-(dimethylamino)acetate;
11) 2-(1-(2-hydroxyethyl)-2,6-dioxopiperidin-3-yl)isoindolin-1,3-dione 2-(diethylamino)acetate;
12) 2-(1-(2-hydroxyethyl)-2,6-dioxopiperidin-3-yl)isoindolin-1,3-dione 2-(1-piperidyl)acetate;
13) 2-(1-(2-hydroxyethyl)-2,6-dioxopiperidin-3-yl)isoindolin-1,3-dione 2-aminoacetate;
14) 2-(1-(2-hydroxyethyl)-2,6-dioxopiperidin-3-yl)isoindolin-1,3-dione (S)-2-aminopropanoate;
15) 2-(1-(2-hydroxyethyl)-2,6-dioxopiperidin-3-yl)isoindolin-1,3-dione (S)-2-amino-3-methylbutanoate;
16) 2-(1-(2-hydroxyethyl)-2,6-dioxopiperidin-3-yl)isoindolin-1,3-dione (S)-2-pyrrolidinecarboxylate;
17) 2-(1-(2-hydroxyethyl)-2,6-dioxopiperidin-3-yl)isoindolin-1,3-dione (S)-2-(2-diethylaminoacetamido)propanoate;
18) 2-(1-(2-hydroxyethyl)-2,6-dioxopiperidin-3-yl)isoindolin-1,3-dione (S)-2-(2-diethylaminoacetamido)-3-methylbutanoate;
19) 2-(1-(2-hydroxyethyl)-2,6-dioxopiperidin-3-yl)isoindolin-1,3-dione (S)-2-amino-3-phenylpropanoate;
20) 2-(1-(4-hydroxybutyl)-2,6-dioxopiperidin-3-yl)isoindolin-1,3-dione 2-(diethylamino)acetate;
21) 4-amino-2-(1-(2-ethoxyethyl)-2,6-dioxopiperidin-3-yl)isoindoline-1,3-dione;
22) 2-(1-(2-hydroxyethyl)-2,6-dioxopiperidin-3-yl)isoindolin-1,3-dione nicotinate;
23) 2-(1-(2-hydroxyethyl)-2,6-dioxopiperidin-3-yl)isoindolin-1,3-dione isonicotinate;
24) 2-(1-(2-hydroxyethyl)-2,6-dioxopiperidin-3-yl)isoindolin-1,3-dione N-ethyl-(S)-2-pyrrolidinecarboxylate;
25) 4-amino-2-(2,6-dioxo-1-(2-propoxyethyl)piperidin-3-yl)isoindoline-1,3-dione;
26) 2-(1-(2-hydroxyethyl)-2,6-dioxopiperidin-3-yl)-5-nitroisoindoline-1,3-dione;
27) 4,5,6,7-tetrafluoro-2-(1-(2-hydroxyethyl)-2,6-dioxopiperidin-3-yl)isoindoline-1,3-dione;
28) 4-amino-2-(1-(2-hydroxyethyl)-2,6-dioxopiperidin-3-yl)isoindolin-1,3-dione nicotinate;
29) 4-amino-2-(1-(2-hydroxyethyl)-2,6-dioxopiperidin-3-yl)isoindolin-1,3-dione acetate;
30) 4-amino-2-(1-(2-hydroxyethyl)-2,6-dioxopiperidin-3-yl)isoindolin-1,3-dione isonicotinate;
31) 4-amino-2-(1-(2-hydroxyethyl)-2,6-dioxopiperidin-3-yl)isoindolin-1,3-dione N-ethyl-(S)-2-pyrrolidinecarboxylate;
32) 4-amino-2-(1-(2-hydroxyethyl)-2,6-dioxopiperidin-3-yl)isoindolin-1,3-dione (S)-2-pyrrolidinecarboxylate;
33) 4-amino-2-(1-(2-hydroxyethyl)-2,6-dioxopiperidin-3-yl)isoindolin-1,3-dione 2-(diethylamino)acetate;
34) 4-amino-2-(1-(2-hydroxyethyl)-2,6-dioxopiperidin-3-yl)isoindolin-1,3-dione 2-(dimethylamino)acetate;
35) 4-amino-2-(1-(2-hydroxyethyl)-2,6-dioxopiperidin-3-yl)isoindolin-1,3-dione 2-(ethylamino)acetate;
36) 4-amino-2-(1-(2-hydroxyethyl)-2,6-dioxopiperidin-3-yl)isoindolin-1,3-dione 2-(methylamino)acetate;
37) 4-amino-2-(1-(2-hydroxyethyl)-2,6-dioxopiperidin-3-yl)isoindolin-1,3-dione 2-aminoacetate;
38) 4-amino-2-(1-(2-hydroxyethyl)-2,6-dioxopiperidin-3-yl)isoindolin-1,3-dione 2-(1-piperidyl)acetate;
39) 4-amino-2-(1-(2-hydroxyethyl)-2,6-dioxopiperidin-3-yl)isoindolin-1,3-dione (S)-2-(diethylamino)propanoate;

40) 4-amino-2-(1-(2-hydroxyethyl)-2,6-dioxopiperidin-3-yl)isoindolin-1,3-dione (S)-2-(dimethylamino)propanoate;
41) 4-amino-2-(1-(2-hydroxyethyl)-2,6-dioxopiperidin-3-yl)isoindolin-1,3-dione (S)-2-ethylaminopropanoate;
42) 4-amino-2-(1-(2-hydroxyethyl)-2,6-dioxopiperidin-3-yl)isoindolin-1,3-dione (S)-2-methylaminopropanoate;
43) 4-amino-2-(1-(2-hydroxyethyl)-2,6-dioxopiperidin-3-yl)isoindolin-1,3-dione (S)-2-aminopropanoate;
44) 4-amino-2-(1-(2-hydroxyethyl)-2,6-dioxopiperidin-3-yl)isoindolin-1,3-dione (S)-2-(pyrrolidin-1-yl)propanoate;
45) 4-amino-2-(1-(2-hydroxyethyl)-2,6-dioxopiperidin-3-yl)isoindolin-1,3-dione (S)-2-(piperidin-1-yl)propanoate;
46) 4-amino-2-(1-(2-hydroxyethyl)-2,6-dioxopiperidin-3-yl)isoindolin-1,3-dione 2-(pyrrolidin-1-yl)acetate;
47) 4-amino-2-(1-(2-hydroxyethyl)-2,6-dioxopiperidin-3-yl)isoindolin-1,3-dione (S)-2-diethylamino-3-methylbutanoate;
48) 4-amino-2-(1-(2-hydroxyethyl)-2,6-dioxopiperidin-3-yl)isoindolin-1,3-dione (S)-2-dimethylamino-3-methylbutanoate;
49) 4-amino-2-(1-(2-hydroxyethyl)-2,6-dioxopiperidin-3-yl)isoindolin-1,3-dione (S)-2-ethylamino-3-methylbutanoate;
50) 4-amino-2-(1-(2-hydroxyethyl)-2,6-dioxopiperidin-3-yl)isoindolin-1,3-dione (S)-2-methylamino-3-methylbutanoate;
51) 4-amino-2-(1-(2-hydroxyethyl)-2,6-dioxopiperidin-3-yl)isoindolin-1,3-dione (S)-2-amino-3-methylbutanoate;
52) 4-amino-2-(1-(2-hydroxyethyl)-2,6-dioxopiperidin-3-yl)isoindolin-1,3-dione (S)-2-pyrrolidin-1-yl-3-methylbutanoate;
53) 4-amino-2-(1-(2-hydroxyethyl)-2,6-dioxopiperidin-3-yl)isoindolin-1,3-dione (S)-2-piperidin-1-yl-3-methylbutanoate;
54) 5-amino-2-(1-(2-hydroxyethyl)-2,6-dioxopiperidin-3-yl)isoindolin-1,3-dione nicotinate;
55) 5-amino-2-(1-(2-hydroxyethyl)-2,6-dioxopiperidin-3-yl)isoindolin-1,3-dione acetate;
56) 5-amino-2-(1-(2-hydroxyethyl)-2,6-dioxopiperidin-3-yl)isoindolin-1,3-dione isonicotinate;
57) 5-amino-2-(1-(2-hydroxyethyl)-2,6-dioxopiperidin-3-yl)isoindolin-1,3-dione N-ethyl-(S)-2-pyrrolidinecarboxylate;
58) 5-amino-2-(1-(2-hydroxyethyl)-2,6-dioxopiperidin-3-yl)isoindolin-1,3-dione (S)-2-pyrrolidinecarboxylate;
59) 5-amino-2-(1-(2-hydroxyethyl)-2,6-dioxopiperidin-3-yl)isoindolin-1,3-dione 2-(diethylamino)acetate;
60) 5-amino-2-(1-(2-hydroxyethyl)-2,6-dioxopiperidin-3-yl)isoindolin-1,3-dione 2-(dimethylamino)acetate;
61) 5-amino-2-(1-(2-hydroxyethyl)-2,6-dioxopiperidin-3-yl)isoindolin-1,3-dione 2-(ethylamino)acetate;
62) 5-amino-2-(1-(2-hydroxyethyl)-2,6-dioxopiperidin-3-yl)isoindolin-1,3-dione 2-(methylamino)acetate;
63) 5-amino-2-(1-(2-hydroxyethyl)-2,6-dioxopiperidin-3-yl)isoindolin-1,3-dione 2-aminoacetate;
64) 5-amino-2-(1-(2-hydroxyethyl)-2,6-dioxopiperidin-3-yl)isoindolin-1,3-dione 2-(1-piperidyl)acetate;
65) 5-amino-2-(1-(2-hydroxyethyl)-2,6-dioxopiperidin-3-yl)isoindolin-1,3-dione (S)-2-(diethylamino)propanoate;
66) 5-amino-2-(1-(2-hydroxyethyl)-2,6-dioxopiperidin-3-yl)isoindolin-1,3-dione (S)-2-(dimethylamino)propanoate;
67) 5-amino-2-(1-(2-hydroxyethyl)-2,6-dioxopiperidin-3-yl)isoindolin-1,3-dione (S)-2-(ethylamino)propanoate;
68) 5-amino-2-(1-(2-hydroxyethyl)-2,6-dioxopiperidin-3-yl)isoindolin-1,3-dione (S)-2-(methylamino)propanoate;
69) 5-amino-2-(1-(2-hydroxyethyl)-2,6-dioxopiperidin-3-yl)isoindolin-1,3-dione (S)-2-aminopropanoate;
70) 5-amino-2-(1-(2-hydroxyethyl)-2,6-dioxopiperidin-3-yl)isoindolin-1,3-dione (S)-2-(pyrrolidin-1-yl)propanoate;
71) 5-amino-2-(1-(2-hydroxyethyl)-2,6-dioxopiperidin-3-yl)isoindolin-1,3-dione (S)-2-(piperidin-1-yl)propanoate;
72) 5-amino-2-(1-(2-hydroxyethyl)-2,6-dioxopiperidin-3-yl)isoindolin-1,3-dione 2-(pyrrolidin-1-yl)acetate
73) 5-amino-2-(1-(2-hydroxyethyl)-2,6-dioxopiperidin-3-yl)isoindolin-1,3-dione (S)-2-diethylamino-3-methylbutanoate;
74) 5-amino-2-(1-(2-hydroxyethyl)-2,6-dioxopiperidin-3-yl)isoindolin-1,3-dione (S)-2-dimethylamino-3-methylbutanoate;
75) 5-amino-2-(1-(2-hydroxyethyl)-2,6-dioxopiperidin-3-yl)isoindolin-1,3-dione (S)-2-ethylamino-3-methylbutanoate;
76) 5-amino-2-(1-(2-hydroxyethyl)-2,6-dioxopiperidin-3-yl)isoindolin-1,3-dione (S)-2-methylamino-3-methylbutanoate;
77) 5-amino-2-(1-(2-hydroxyethyl)-2,6-dioxopiperidin-3-yl)isoindolin-1,3-dione (S)-2-amino-3-methylbutanoate;
78) 5-amino-2-(1-(2-hydroxyethyl)-2,6-dioxopiperidin-3-yl)isoindolin-1,3-dione (S)-2-pyrrolidin-1-yl-3-methylbutanoate;
79) 5-amino-2-(1-(2-hydroxyethyl)-2,6-dioxopiperidin-3-yl)isoindolin-1,3-dione (S)-2-piperidin-1-yl-3-methylbutanoate;
80) 4-fluoro-2-(1-(2-hydroxyethyl)-2,6-dioxopiperidin-3-yl)isoindolin-1,3-dione nicotinate;
81) 4-fluoro-2-(1-(2-hydroxyethyl)-2,6-dioxopiperidin-3-yl)isoindolin-1,3-dione acetate;
82) 4-fluoro-2-(1-(2-hydroxyethyl)-2,6-dioxopiperidin-3-yl)isoindolin-1,3-dione isonicotinate;
83) 4-fluoro-2-(1-(2-hydroxyethyl)-2,6-dioxopiperidin-3-yl)isoindolin-1,3-dione N-ethyl-(S)-2-pyrrolidinecarboxylate;
84) 4-fluoro-2-(1-(2-hydroxyethyl)-2,6-dioxopiperidin-3-yl)isoindolin-1,3-dione (S)-2-pyrrolidinecarboxylate;
85) 4-fluoro-2-(1-(2-hydroxyethyl)-2,6-dioxopiperidin-3-yl)isoindolin-1,3-dione 2-(diethylamino)acetate;
86) 4-fluoro-2-(1-(2-hydroxyethyl)-2,6-dioxopiperidin-3-yl)isoindolin-1,3-dione 2-(dimethylamino)acetate;
87) 4-fluoro-2-(1-(2-hydroxyethyl)-2,6-dioxopiperidin-3-yl)isoindolin-1,3-dione 2-(ethylamino)acetate;
88) 4-fluoro-2-(1-(2-hydroxyethyl)-2,6-dioxopiperidin-3-yl)isoindolin-1,3-dione 2-(methylamino)acetate;
89) 4-fluoro-2-(1-(2-hydroxyethyl)-2,6-dioxopiperidin-3-yl)isoindolin-1,3-dione 2-aminoacetate;
90) 4-fluoro-2-(1-(2-hydroxyethyl)-2,6-dioxopiperidin-3-yl)isoindolin-1,3-dione 2-(1-piperidyl)acetate;
91) 4-fluoro-2-(1-(2-hydroxyethyl)-2,6-dioxopiperidin-3-yl)isoindolin-1,3-dione (S)-2-(diethylamino)propanoate;
92) 4-fluoro-2-(1-(2-hydroxyethyl)-2,6-dioxopiperidin-3-yl)isoindolin-1,3-dione (S)-2-(dimethylamino)propanoate;
93) 4-fluoro-2-(1-(2-hydroxyethyl)-2,6-dioxopiperidin-3-yl)isoindolin-1,3-dione (S)-2-ethylaminopropanoate;
94) 4-fluoro-2-(1-(2-hydroxyethyl)-2,6-dioxopiperidin-3-yl)isoindolin-1,3-dione (S)-2-methylaminopropanoate;
95) 4-fluoro-2-(1-(2-hydroxyethyl)-2,6-dioxopiperidin-3-yl)isoindolin-1,3-dione (S)-2-aminopropanoate;
96) 4-fluoro-2-(1-(2-hydroxyethyl)-2,6-dioxopiperidin-3-yl)isoindolin-1,3-dione (S)-2-(pyrrolidin-1-yl)propanoate;

97) 4-fluoro-2-(1-(2-hydroxyethyl)-2,6-dioxopiperidin-3-yl) isoindolin-1,3-dione (S)-2-(piperidin-1-yl)propanoate;
98) 4-fluoro-2-(1-(2-hydroxyethyl)-2,6-dioxopiperidin-3-yl) isoindolin-1,3-dione 2-(pyrrolidin-1-yl)acetate;
99) 4-fluoro-2-(1-(2-hydroxyethyl)-2,6-dioxopiperidin-3-yl) isoindolin-1,3-dione (S)-2-diethylamino-3-methylbutanoate;
100) 4-fluoro-2-(1-(2-hydroxyethyl)-2,6-dioxopiperidin-3-yl)isoindolin-1,3-dione (S)-2-dimethylamino-3-methylbutanoate;
101) 4-fluoro-2-(1-(2-hydroxyethyl)-2,6-dioxopiperidin-3-yl)isoindolin-1,3-dione (S)-2-ethylamino-3-methylbutanoate;
102) 4-fluoro-2-(1-(2-hydroxyethyl)-2,6-dioxopiperidin-3-yl)isoindolin-1,3-dione (S)-2-methylamino-3-methylbutanoate;
103) 4-fluoro-2-(1-(2-hydroxyethyl)-2,6-dioxopiperidin-3-yl)isoindolin-1,3-dione (S)-2-amino-3-methylbutanoate;
104) 4-fluoro-2-(1-(2-hydroxyethyl)-2,6-dioxopiperidin-3-yl)isoindolin-1,3-dione (S)-2-pyrrolidin-1-yl-3-methylbutanoate;
105) 4-fluoro-2-(1-(2-hydroxyethyl)-2,6-dioxopiperidin-3-yl)isoindolin-1,3-dione (S)-2-piperidin-1-yl-3-methylbutanoate;
106) 4-fluoro-2-(1-(2-hydroxyethyl)-2,6-dioxopiperidin-3-yl)isoindolin-1,3-dione N-methyl-(S)-2-pyrrolidinecarboxylate;
107) 4-amino-2-(1-(2-hydroxyethyl)-2,6-dioxopiperidin-3-yl)isoindolin-1,3-dione N-methyl-(S)-2-pyrrolidinecarboxylate;
108) 5-amino-2-(1-(2-hydroxyethyl)-2,6-dioxopiperidin-3-yl)isoindolin-1,3-dione N-methyl-(S)-2-pyrrolidinecarboxylate;
109) 2-(1-(2-hydroxyethyl)-2,6-dioxopiperidin-3-yl)-4-(methylamino)isoindoline-1,3-dione;
110) 4-(dimethylamino)-2-(1-(2-hydroxyethyl)-2,6-dioxopiperidin-3-yl)isoindoline-1,3-dione;
111) 4-(methylamino)-2-(2,6-dioxo-1-(2-propoxyethyl)piperidin-3-yl)isoindoline-1,3-dione;
112) 2-(1-(2-methoxyethyl)-2,6-dioxopiperidin-3-yl)-4-(methylamino)isoindoline-1,3-dione;
113) 2-(1-(2-ethoxyethyl)-2,6-dioxopiperidin-3-yl)-4-(methylamino)isoindoline-1,3-dione;
114) N-(2-(1-(2-methoxyethyl)-2,6-dioxopiperidin-3-yl)-1,3-dioxoisoindolin-7-yl)acetamide;
115) 4-(dimethylamino)-2-(1-(2-methoxyethyl)-2,6-dioxopiperidin-3-yl)isoindoline-1,3-dione;
116) 4-(dimethylamino)-2-(1-(2-ethoxyethyl)-2,6-dioxopiperidin-3-yl)isoindoline-1,3-dione;
117) 4-(dimethylamino)-2-(1-(3-hydroxypropyl)-2,6-dioxopiperidin-3-yl)isoindoline-1,3-dione;
118) 4-(dimethylamino)-2-(1-(3-methoxypropyl)-2,6-dioxopiperidin-3-yl)isoindoline-1,3-dione;
119) 4-amino-2-(1-(3-methoxypropyl)-2,6-dioxopiperidin-3-yl)isoindoline-1,3-dione;
120) 4-amino-2-(1-(3-hydroxypropyl)-2,6-dioxopiperidin-3-yl)isoindoline-1,3-dione;
121) 5-amino-2-(1-(3-methoxypropyl)-2,6-dioxopiperidin-3-yl)isoindoline-1,3-dione;
122) 4-(methylamino)-2-(1-(2-hydroxyethyl)-2,6-dioxopiperidin-3-yl)isoindolin-1,3-dione nicotinate;
123) 4-(methylamino)-2-(1-(2-hydroxyethyl)-2,6-dioxopiperidin-3-yl)isoindolin-1,3-dione acetate;
124) 4-(methylamino)-2-(1-(2-hydroxyethyl)-2,6-dioxopiperidin-3-yl)isoindolin-1,3-dione isonicotinate;
125) 4-(methylamino)-2-(1-(2-hydroxyethyl)-2,6-dioxopiperidin-3-yl)isoindolin-1,3-dione N-ethyl-(S)-2-pyrrolidinecarboxylate;
126) 4-(methylamino)-2-(1-(2-hydroxyethyl)-2,6-dioxopiperidin-3-yl)isoindolin-1,3-dione (S)-2-pyrrolidinecarboxylate;
127) 4-(methylamino)-2-(1-(2-hydroxyethyl)-2,6-dioxopiperidin-3-yl)isoindolin-1,3-dione 2-(diethylamino)acetate;
128) 4-(methylamino)-2-(1-(2-hydroxyethyl)-2,6-dioxopiperidin-3-yl)isoindolin-1,3-dione 2-(dimethylamino)acetate;
129) 4-(methylamino)-2-(1-(2-hydroxyethyl)-2,6-dioxopiperidin-3-yl)isoindolin-1,3-dione 2-(ethylamino)acetate;
130) 4-(methylamino)-2-(1-(2-hydroxyethyl)-2,6-dioxopiperidin-3-yl)isoindolin-1,3-dione 2-(methylamino)acetate;
131) 4-(methylamino)-2-(1-(2-hydroxyethyl)-2,6-dioxopiperidin-3-yl)isoindolin-1,3-dione 2-aminoacetate;
132) 4-(methylamino)-2-(1-(2-hydroxyethyl)-2,6-dioxopiperidin-3-yl)isoindolin-1,3-dione 2-(1-piperidyl)acetate;
133) 4-(methylamino)-2-(1-(2-hydroxyethyl)-2,6-dioxopiperidin-3-yl)isoindolin-1,3-dione (S)-2-amino-3-methylbutanoate; and
134) 4-(methylamino)-2-(1-(2-hydroxyethyl)-2,6-dioxopiperidin-3-yl)isoindolin-1,3-dione (S)-2-aminopropanoate.

The compound of the invention shown in formula (I) and used as a pharmaceutically active ingredient may be a single enantiomer (R or S) or racemate.

The compounds of this invention shown in formula (I) may be used as pharmaceutically-active ingredients in various forms, for example, free bases, inorganic acid salts, which includes hydrochloride, sulfate, nitrate, phosphate, and also organic salts, which includes sulfonate, acetate, formate, fumarate, maleate, citrate, tartrate, malate, benzoate, ascorbate, gluconate, lactate, succinate and trifluoroacetate.

In other aspects, this invention is directed at a method to prepare the compounds of the general formula (I), by reacting compounds bearing general formula (VI),

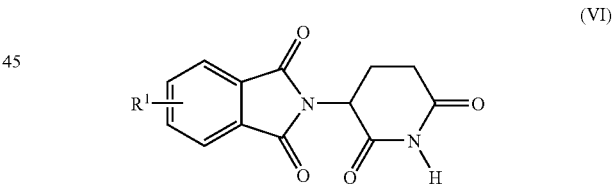

(VI)

with Z—CH$_2$(CH$_2$)$_n$—R$^2$ wherein R$^1$ represents from one to four of the same or different substituents selected from F, Cl, Br, NO$_2$, H, C$_{1-4}$ alkyl, OR$^3$, NR$^3$R$^4$; n represents 1, 2, 3, 4, 5, or 6; R$^2$ represents OR$^3$, NR$^3$R$^4$, N(R$^3$)COR$^4$, O$_2$CR$^5$; R$^3$ and R$^4$ represent independently and at each occurrence H, or C$_{1-4}$ alkyl; R$^5$ represents CHR$^6$NR$^7$R$^8$, CHR$^6$NR$^9$C(O)CHR$^{10}$NR$^7$R$^8$, W, or CHR$^6$NR$^9$C(O)W; R$^6$, R$^9$ and R$^{10}$ independently and at each occurrence represent H, C$_{1-4}$ alkyl; R$^7$ and R$^8$ independently and at each occurrence represent H, C$_{1-4}$ alkyl, or R$^7$ and R$^8$ taken together represent 1,3-propylene, 1,4-butylene, 1,5-pentylene, or 1,6-hexylene; W represents four-membered, five-membered, six-membered, seven-membered or eight-membered saturated or unsaturated heterocycles, particularly 2-pyridyl, 3-pyridyl, 4-pyridyl, 2-pyrimidinyl, 3-pyrimidinyl, 4-pyrimidinyl, or heterocycles of the formula (II), (III), (IV) or (V);

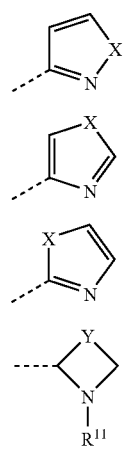

X represents O, S, or NR$^{12}$; Y represents substituents such as 1,2-ethylene, 1,3-propylene, 1,4-butylene, 1,5-pentylene, 1,6-hexylene, —CH$_2$OCH$_2$—, —CH$_2$SCH$_2$—, or —CH$_2$NR$^{12}$CH$_2$—; and R$^{11}$ and R$^{12}$ each independently and at each occurrence represent H, or C$_{1-4}$ alkyl; Z represents Cl, Br.

In a method to prepare the compounds of the general formula (I), the ratio of a compound shown in Formula (VI) to Z—CH$_2$(CH$_2$)$_n$—R$^2$ may be between 3:1 and 1:3.

The synthesis may be facilitated by an inorganic base, which includes but is not limited to NaH, KH, CaH$_2$, K$_2$CO$_3$, Na$_2$CO$_3$, KHCO$_3$, NaHCO$_3$, Li$_2$CO$_3$, Cs$_2$CO$_3$, LiOH, KOH, NaOH, Ca (OH)$_2$, K$_3$PO$_4$, K$_2$HPO$_4$, or an organic base. The proportion of base to substrate is from 50% (mole) to 300% (mole). The reactions are conducted in an organic solvent, such as dichloromethane, chloroform, acetone, butanone, dimethylformamide, dimethylsulfoxide, ethylene glycol dimethyl ether, tetrahydrofuran, pyridine or acetonitrile, and may be conducted under heterogeneous conditions, especially with a phase-transfer catalyst.

The compounds of formula (I) are indicated for and are useful in the treatment and prevention of diseases which are associated with decreased TNFα levels in patients, including, but not limited to inflammatory or infectious diseases, diseases of the immune system, or malignant tumors. Particularly, these diseases include but are not limited to septic shock, endotoxic shock, hemodynamic shock, septic syndrom, post ischemic reperfusion injury, malaria, mycobacterial infection, meningitis, psoriasis, congestive heart failure, fibrotic disease, cachexia, transplant immune rejection, cancer, autoimmune disease, opportunistic infection in AIDS, erythema nodosum leprosum, lupus erythematosus, intractable lupus erythematosus, Behcet syndrome, regional ileitis, myelodysplastic syndrome, rheumatoid arthritis (RA), hepatitis, nephritis, rheumatoid spondylitis, multiple myeloma, thyroma, renal cancer, prostate carcinoma, lymphoma, leukemia, and hepatoma.

Except for at least one kind of compounds of formula (I), the pharmaceutical compositions of the invention may comprise one or more carrier materials, bulking agents, solvents, diluents, colorants, and/or adhesives. The selection of adjuvants and dosage is decided taking into account the mode of administration, e.g., gastrointestinal, intravenous, abdominal, dermal, intramuscular, nasal, ocular, pulmonary, anal, vaginal, transdermal, etc.

The pharmaceutical compositions and pharmaceutically active compounds of the invention may be used in combination with other appropriate pharmaceutically active compounds and/or pharmaceutical compositions.

BRIEF DESCRIPTION OF THE DRAWINGS

FIGS. 1-9 illustrate chemical structures of piperidine-2,6-dione derivatives according to the invention; and FIGS. 10-11 illustrate chemical structures of intermediates in the synthesis of piperidine-2,6-dione derivatives and chemical structures of piperidine-2,6-dione derivatives according to the invention.

DETAILED DESCRIPTION OF THE INVENTION

Specific Implementation Method

Figure 1:
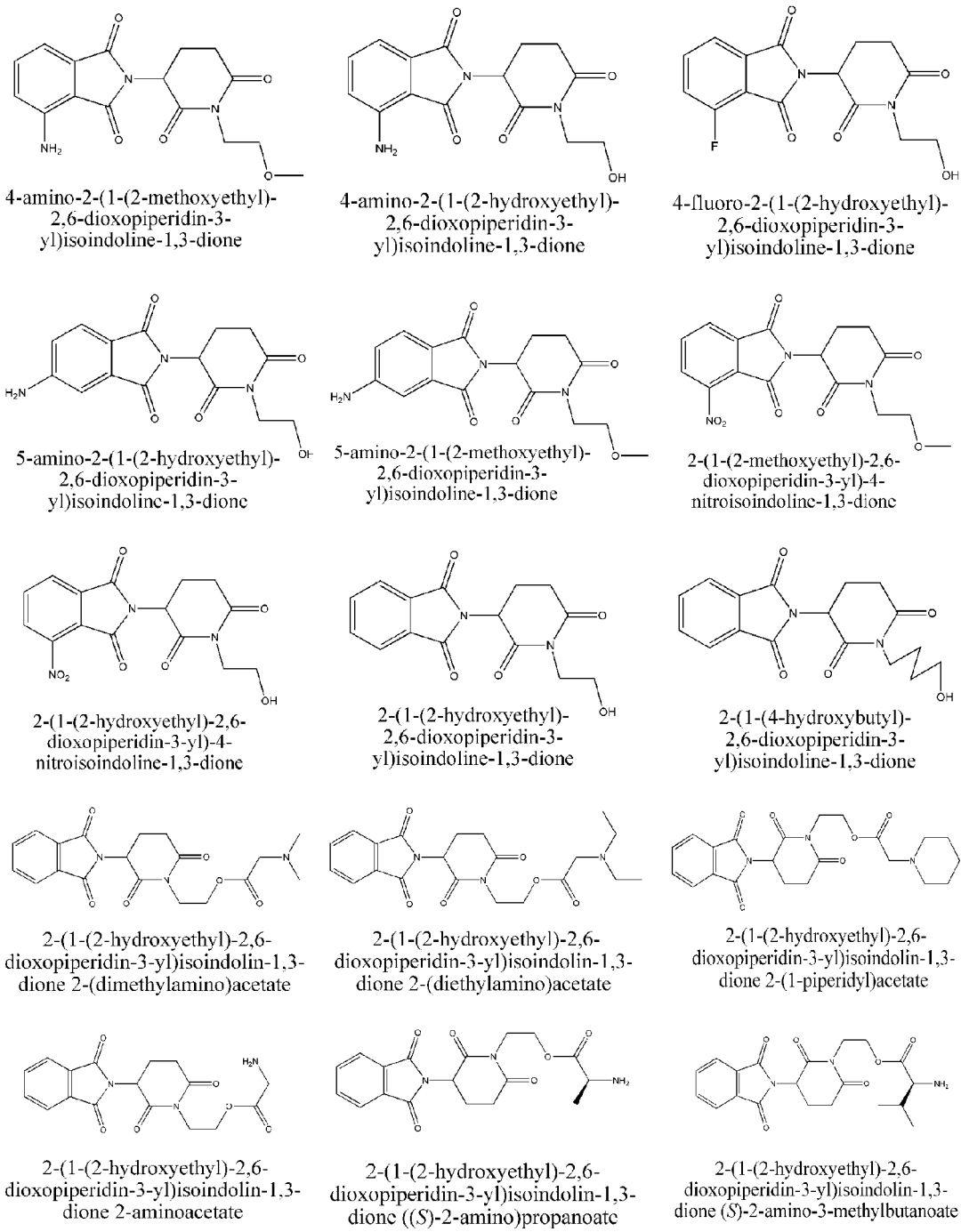
Figure 5:
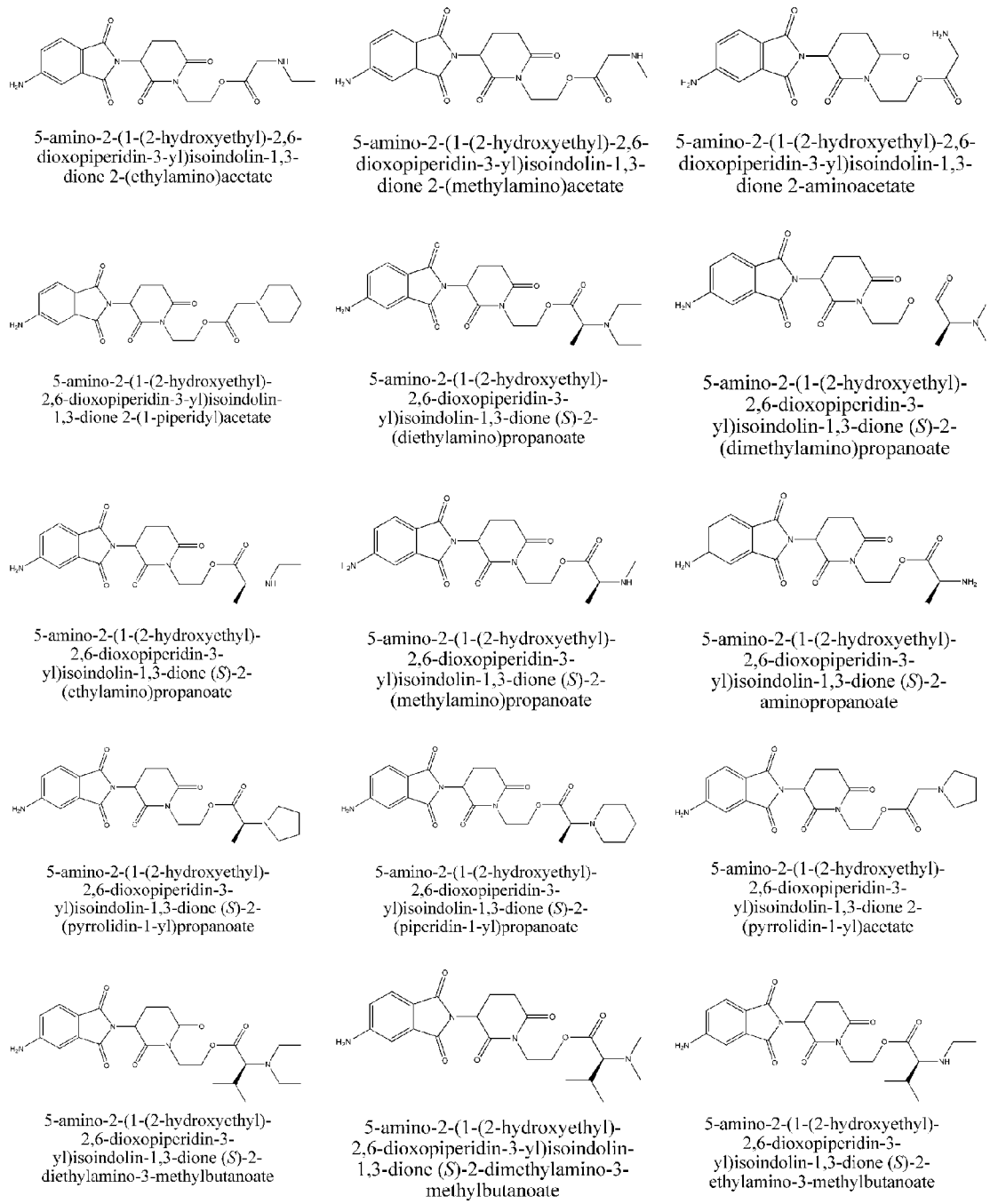

Pharmacological Research: Effects of Monocyte (PBMC) Stimulation by LPS on TNFα

Cytokine TNFα released by PBMCs in peripheral blood after lip polysaccharide (LPS) stimulation in vitro was studied. The followings are research methods of cytokine TNFα released by PBMCs, which are inhibited by compounds of the invention.

PBMCs were obtained from blood of at least three volunteers after heparin treatment, by the method of gradient extraction. PBMCs were collected and washed with 1640 culture medium three times (10% calf serum, 2 mM L-glutamine, 100 mM mercaptoethanol, 50 µg/ml streptomycin, 50 U/ml penicillin). The above PBMCs were placed onto a 24-well cell culture plate. The concentration was adjusted to 1×10$^6$ cells/ml with 1640 culture medium. Test compounds were dissolved in dimethylsulfoxide at an appropriate concentration. The resultant solution was added to the above cell culture medium and the culture plate was placed in a CO$_2$ incubator (5% CO$_2$, 90% humidity) for 1 hour. Then, LPS (Sigma) was added to adjust the concentration to 0.1 µg/ml (except for contrast). After 20 hrs of incubation, the content of TNFα in supernatant of the above PBMC culture medium was determined by ELISA kit (America Genzyme Co) using standard method. The measured value of the control (no active compound), and the measured value of the tested compounds was used to calculate the TNFα inhibition rate. The concentration of compounds giving a 50% TNFα inhibition (IC$_{50}$ value) was calculated by nonlinear regression analysis. Each concentration was determined twice and an average value was obtained. Results are illustrated in Table 1.

TABLE 1

Inhibit LPS to stimulate monocytes to inhibit TNFα activity

| Compound | Concentration (µM) | Inhibition Degree (%) | EC$_{50}$ (µM) |
|---|---|---|---|
| Thalidomide | 100 | 22 | 183 |
| of example 1 | 3.0 | 70 | |
| of example 9 | 3.0 | 20 | |
| of example 22 | 3.0 | 18 | |
| of example 24 | 3.0 | 28 | |
| of example 26 | 3.0 | 95 | 0.25 |
| of example 27 | 3.0 | 92 | 0.3 |
| of example 28 | 3.0 | 78 | |
| of example 29 | 3.0 | 64 | |
| of example 30 | 3.0 | 58 | |
| of example 31 | 3.0 | 62 | |

EXAMPLES

Abbreviations

DCC: dicyclohexylcarbodiimide; DCM: dichloromethane; TFA: trifluoroacetic acid;

CDCl$_3$: deuterochloroform; HCl: hydrogen chloride; DMAP: 4-(N,N-dimethylamino)pyridine; TEA: triethylamine.

Example 1

2-(1-(2-Hydroxyethyl)-2,6-dioxopiperidin-3-yl) isoindoline-1,3-dione 2-(2,6-Dioxopiperidin-3-yl)isoindoline-1,3-dione (2.5 g) was dissolved in DMF (dry, 60 mL). 95% NaH (0.24 g) was added. The mixture was stirred for 30 minutes at room temperature. Then, chloroethanol (0.68 mL) was added, and the mixture was stirred over night at room temperature. The reaction mixture was diluted with 300 mL of water and extracted with ethyl acetate (3×60 mL). Organic phases were combined and washed twice with water, and once with brine, then dried over anhydrous magnesium sulfate. Rotary evaporation of solvent yielded crude product, which was purified by silica gel column chromatography (acetic ether:petroleum ether=1:1) to yield 1.1 g of pure title product. $^1$H NMR (CDCl$_3$, ppm) δ 7.88-7.90 (m, 2H), 7.77-7.79 (m, 2H), 5.06 (dd, 1H, J=5.6, 12.4 Hz), 4.02-4.12 (m, 2H), 3.76-3.80 (m, 2H), 2.94-3.02 (m, 1H), 2.72-2.90 (m, 2H), 2.29-2.31 (m, 1H), 2.14-2.23 (m, 1H).

Example 2

2-(1-(2-hydroxyethyl)-2,6-dioxopiperidin-3-yl)isoindolin-1,3-dione (S)-2-(tert-butoxycarbonylamino)-3-methylbutanoate (S)-2-Boc-amino-3-methyl butyric acid (1.03 g), 2-(1-(2-Hydroxyethyl)-2,6-dioxopiperidin-3-yl)isoindoline-1,3-dione (1.51 g), and DMAP (20 mg) were dissolved in DCM (30 mL). The mixture was magnetically stirred at room temperature. DCC (1.10 g) was added in one portion and the mixture was reacted overnight. The mixture was filtered to remove dicyclohexylurea. The filter cake washed several times with DCM. The combined filtrates were washed three times with saturated sodium bicarbonate solution and once with brine (30 mL), dried over anhydrous magnesium sulfate and filtrated. The solvent was removed by rotary evaporation in vacuo. A white solid (430 mg) was obtained after silica gel column purification (50% acetic ether/petroleum ether).

Example 3

2-(1-(2-hydroxyethyl)-2,6-dioxopiperidin-3-yl)isoindolin-1,3-dione (S)-2-amino-3-methylbutanoate 2-(1-(2-hydroxyethyl)-2,6-dioxopiperidin-3-yl)isoindolin-1,3-dione (S)-2-(tert-butoxycarbonylamino)-3-methylbutanoate (410 mg) was dissolved in 30% TFA/DCM (5 mL), the mixture was stirred on a magnetic stirrer for 4 hrs at room temperature. White foam was obtained after reduced pressure distillation to distill off the solvent. The foam was dissolved in DCM (30 mL). The resultant solution washed with aqueous saturated sodium bicarbonate solution and brine (30 mL), dried over anhydrous magnesium sulfate, and filtered. Title compound was obtained as a white solid (260 mg) after rotary evaporation. $^1$H NMR (CDCl$_3$, ppm) δ 7.87-7.91 (m, 2H), 7.76-7.79 (m, 2H), 4.97-5.08 (m, 1H), 4.38-4.43 (m, 1H), 4.05-4.30 (m, 3H), 3.25 (dd, 1H, J=4.8, 13.2 Hz), 2.95-3.05 (m, 1H), 2.80-2.95 (m, 2H), 2.10-2.20 (m, 1H), 1.90-2.10 (m, 2H), 1.00-1.20 (m, 1H), 0.95-0.98 (m, 3H), 0.87-0.91 (m, 3H). MS (m/e): 402 (M+H$^+$).

Example 4

2,5-Dioxopyrrolidinyl bromoacetate

Bromoacetic acid (4.30 g) and N-hydroxysuccinimide (4.03 g) were dissolved in DCM (25 ml). The mixture was stirred on a magnetic stirrer at room temperature. DCC was added (7.42 g) in one portion and the mixture was reacted overnight. The reaction mixture was filtered to remove dicyclohexylurea. The filter cake washed several times with DCM. The combined filtrates were washed three times with saturated aqueous sodium chloride solution (30 mL/each wash), dried over anhydrous magnesium sulfate, and filtered. The title compound was obtained as a white solid (5 g) after rotary evaporation in vacuo.

Example 5

2-(1-(2-hydroxyethyl)-2,6-dioxopiperidin-3-yl)isoindolin-1,3-dione (S)-2-(2-bromoacetamido)-3-methylbutanoate 2-(1-(2-hydroxyethyl)-2,6-dioxopiperidin-3-yl)isoindolin-1,3-dione (S)-2-amino-3-methylbutanoate (1.8 g) was dissolved in DCM (20 mL). 2,5-Dioxopyrrolidinyl bromoacetate (1.04 g) was added to the mixture. The mixture was stirred with a magnetic stirrer at room temperature, and reacted overnight. The solvent was stripped in vacuo. White solid (1.3 g) was obtained after purification of the crude product on silica gel column (eluted with acetic ether:petroleum ether=1:1).

Example 6

2-(1-(2-hydroxyethyl)-2,6-dioxopiperidin-3-yl)isoindolin-1,3-dione (S)-2-(2-diethylaminoacetamido)-3-methylbutanoate 2-(1-(2-hydroxyethyl)-2,6-dioxopiperidin-3-yl)isoindolin-1,3-dione (S)-2-(2-bromoacetamido)-3-methylbutanoate (120 mg) was dissolved in DCM (8 mL). The mixture was stirred and diethylamine solution was added slowly dropwise (0.04 mL). The reaction mixture was stirred additionally for 2 hrs at room temperature. The solvent and the residual diethylamine were removed by rotary evaporation in vacuo. 101 mg of white solid were obtained after purification of the crude product by silica gel column chromatography (eluted with acetic ether:petroleum ether=3:1). $^1$H NMR (CDCl$_3$, ppm) δ 7.94 (d, 1H, J=8.4 Hz), 7.87-7.91 (m, 2H), 7.76-7.79 (m, 2H), 4.97-5.08 (m, 1H), 4.38-4.43 (m, 1H), 4.05-4.30 (m, 3H), 3.25 (dd, 1H, J=4.8, 13.2 Hz), 3.05 (s, 2H), 2.95-3.05 (m, 1H), 2.80-2.95 (m, 2H), 2.45-2.58 (m, 4H), 2.10-2.20 (m, 1H), 1.90-2.10 (m, 2H), 1.00-1.20 (m, 7H), 0.95-0.98 (m, 3H), 0.87-0.91 (m, 3H).

Example 7

2-(1-(2-hydroxyethyl)-2,6-dioxopiperidin-3-yl)isoindolin-1,3-dione (S)-2-(2-diethylaminoacetamido)-3-methylbutanoate hydrochloride The compound (76 mg) obtained from example 6 was dissolved in DCM (10 mL) and 15% HCl/methanol solution (5 mL) were added dropwise. The solvent was eliminated by rotary evaporation in vacuo and then white solid (82 mg) was obtained.

Example 8

2-(1-(2-hydroxyethyl)-2,6-dioxopiperidin-3-yl)isoindolin-1,3-dione bromoacetate Bromoacetic acid (138.95 mg) and 2-(1-(2-hydroxyethyl)-2,6-dioxopiperidin-3-yl)isoindoline-1,3-dione (288 mg)

were dissolved in DCM (20 mL). The mixture was stirred on a magnetic stirrer at room temperature. DCC (206 mg) was added in one portion. The mixture was allowed to react overnight. Then, the mixture was filtered to remove dicyclohexylurea. The filter cake washed several times with DCM. The filtrates were combined and then washed three times with brine (30 mL/wash), dried over anhydrous magnesium sulfate, and filtered. The solvent was eliminated by rotary evaporation in vacuo and then white solid (390 mg) was obtained. $^1$H NMR (CDCl$_3$, ppm) δ 7.88-7.90 (m, 2H), 7.77-7.79 (m, 2H), 4.96-5.08 (m, 1H), 4.85 (s, 2H), 4.02-4.12 (m, 2H), 3.76-3.80 (m, 2H), 2.94-3.02 (m, 1H), 2.72-2.90 (m, 2H), 2.14-2.23 (m, 1H).

Example 9

2-(1-(2-hydroxyethyl)-2,6-dioxopiperidin-3-yl)isoindolin-1,3-dione 2-(diethylamino)acetate 2-(1-(2-hydroxyethyl)-2,6-dioxopiperidin-3-yl)isoindolin-1,3-dione bromoacetate (409 mg) was dissolved in DMF (10 mL). Potassium carbonate powder (800 mg) was added. Diethylamine solution (0.4 mL) was added dropwise while stirring. The reaction mixture was stirred for 24 hrs at room temperature. The solvent and the residual diethylamine were removed by rotary evaporation in vacuo. The resultant solid mixture was subjected to silica gel column chromatography (eluted with acetic ether:petroleum ether=2:1) and then a white solid (128 mg) was obtained. $^1$H NMR (CDCl$_3$, ppm) δ 7.87-7.90 (m, 2H), 7.76-7.79 (m, 2H), 4.97-5.04 (m, 1H), 4.28-4.33 (m, 2H), 4.08-4.16 (m, 2H), 3.30 (s, 2H), 2.97-3.02 (m, 1H), 2.76-2.85 (m, 2H), 2.61-2.68 (m, 4H), 2.10-2.14 (m, 1H), 1.02-1.06 (m, 6H). MS (m/e): 416 (M+H$^+$).

Example 10

2-(1-(2-hydroxyethyl)-2,6-dioxopiperidin-3-yl)isoindolin-1,3-dione 2-(diethylamino)acetate hydrochloride The compound obtained from example 9 (76 mg) was dissolved in DCM (10 mL), and 15% HCl/methanol solution (10 mL) was added dropwise. The solvent was removed by rotary evaporation in vacuo to afford white solid (80 mg). Solubility of this compound in water was higher than 100 mg/mL.

Example 11

2-(1-(2-hydroxyethyl)-2,6-dioxopiperidin-3-yl)isoindolin-1,3-dione 2-(dimethylamino)acetate The title compound was obtained by the method described in example 9 with dimethylamine instead of diethylamine. $^1$H NMR (CDCl$_3$, ppm) δ 7.87-7.90 (m, 2H), 7.76-7.79(m, 2H), 4.97-5.08(m, 1H), 4.28-4.33(m, 2H), 4.08-4.16(m, 2H), 3.30 (s, 2H), 2.97-3.02(m, 1H), 2.76-2.85(m, 2H), 2.31(s, 6H), 2.10-2.14(m, 1H).

Example 12

2-(1-(2-hydroxyethyl)-2,6-dioxopiperidin-3-yl)isoindolin-1,3-dione 2-(dimethylamino)acetate hydrochloride The title compound was obtained by the method of described in example ten with the title compound of example 11 as a starting material. The solubility of the title compound of this example was higher than 100 mg/mL in water.

Example 13

2-(1-(2-hydroxyethyl)-2,6-dioxopiperidin-3-yl)isoindolin-1,3-dione 2-(1-piperidyl)acetate The title compound was obtained by the method described in example 9 with piperidine in place of diethylamine. $^1$H NMR (CDCl$_3$, ppm) δ 7.87-7.90 (m, 2H), 7.76-7.79 (m, 2H), 4.97-5.08 (m, 1H), 4.28-4.33 (m, 2H), 4.08-4.16 (m, 2H), 3.30 (s, 2H), 2.97-3.02 (m, 1H), 2.76-2.85 (m, 2H), 2.31 (s, 6H), 2.10-2.14 (m, 1H).

Example 14

2-(1-(2-hydroxyethyl)-2,6-dioxopiperidin-3-yl)isoindolin-1,3-dione 2-(1-piperidyl)acetate hydrochloride The title compound was obtained by the method described in example 10 with the title compound of example 13 as starting material. The solubility of the title compound of this example in water was more than 100 mg/mL.

Example 15

2-(1-(2-hydroxyethyl)-2,6-dioxopiperidin-3-yl)isoindolin-1,3-dione (S)-2-(diethylamino)-3-methylbutanoate 2-(1-(2-hydroxyethyl)-2,6-dioxopiperidin-3-yl)isoindolin-1,3-dione (S)-2-amino-3-methylbutanoate (92 mg) was dissolved in acetonitrile (18 mL). Ethyl iodide (74 mg) was added. The mixture was stirred at 80° C. and allowed to react overnight. The solvent was removed by rotary evaporation in vacuo. White solid (30 mg) was obtained after the crude product was purified by silica gel column (eluted with acetic ether:petroleum ether=1:1). $^1$H NMR (CDCl$_3$, ppm) δ 7.86-7.90 (m, 2H), 7.76-7.79 (m, 2H), 4.97-5.08 (m, 1H), 4.38-4.43 (m, 1H), 4.05-4.30 (m, 3H), 3.15-3.25 (m, 1H), 2.95-3.05 (m, 1H), 2.80-2.95 (m, 2H), 2.45-2.58 (m, 4H), 2.10-2.20 (m, 1H), 1.90-2.10 (m, 2H), 1.00-1.20 (m, 7H), 0.95-0.98 (m, 3H), 0.87-0.91 (m, 3H).

Example 16

2-(1-(2-hydroxyethyl)-2,6-dioxopiperidin-3-yl)isoindolin-1,3-dione N-tert-butoxycarbonyl-(S)-2-pyrrolidinecarboxylate (S)-1-(tert-butoxycarbonyl)pyrrolidine-2-carboxylic acid (374 mg) and 2-(1-(2-hydroxyethyl)-2,6-dioxopiperidin-3-yl)isoindoline-1,3-dione (500 mg) were dissolved in DCM (30 mL). The mixture was stirred on a magnetic stirrer at room temperature. DCC (350 mg) and DMAP (25 mg) were added in one portion and the mixture was allowed to react overnight. The mixture was then filtered to remove dicyclohexylurea. The filter cake washed several times with DCM, and the filtrates were combined. The filtrates were dried over anhydrous magnesium sulfate and filtered. The solvent was removed by rotary evaporation in vacuo. White solid (658 mg) was obtained after the crude product was purified by silica gel column chromatography (eluted with chloroform:acetone 9:2).

Example 17

2-(1-(2-hydroxyethyl)-2,6-dioxopiperidin-3-yl)isoindolin-1,3-dione (S)-2-pyrrolidinecarboxylate The compound obtained in example 16 (658 mg) was dissolved in 25% TFA/DCM solution (10 mL). The mixture was stirred on a magnetic stirrer for 4 hrs at room temperature. DCM and most of TFA were removed by rotary evaporation in vacuo. The foam obtained was dissolved in DCM (50 mL). The resultant mixture was washed with saturated sodium bicarbonate solution and brine, dried over anhydrous magnesium sulfate, and filtered. The solid obtained (380 mg) was dried in vacuo. $^1$H NMR (CDCl$_3$, ppm) δ 8.0-8.1 (m, 2H), 7.90-8.00 (m, 2H), 5.20-5.28 (m, 1H), 4.59-4.62 (m, 1H), 4.30-4.55 (m, 2H), 4.00-4.30 (m, 2H), 3.70-3.85 (m,1H), 3.40-3.65 (m, 2H), 2.90-3.12 (m, 2H), 2.70-2.90 (m, 1H), 2.30-2.50 (m, 1H), 2.00-2.20 (m, 4H)

Example 18

2-(1-(2-hydroxyethyl)-2,6-dioxopiperidin-3-yl)isoindolin-1,3-dione (S)-2-(nicotinamido)-3-methylbutanoate 2-(1-(2-hydroxyethyl)-2,6-dioxopiperidin-3-yl)isoindolin-1,3-dione (S)-2-amino-3-methylbutanoate (200 mg) and 2,5-dioxopyrrolidinyl nicotinate (120 mg) were dissolved in DCM (20 mL). The mixture was stirred on a magnetic stirrer at room temperature. Triethylamine (1 mL) was added in one portion and the mixture was allowed to react overnight. The reaction mixture was then poured into DCM (30 mL), washed with saturated sodium bicarbonate solution three times (30 mL/wash) and brine (30 mL), dried with anhydrous magnesium sulfate, and filtered. The solvent was removed by rotary evaporation in vacuo. The crude product was purified by silica gel column chromatography (eluted with chloroform:acetone=5:2) to yield pure title compound (239 mg). $^1$HNMR (CDCl$_3$, ppm) δ 9.04 (d, 1H, J=11.2 Hz), 8.72 (s, 1H), 8.13 (d, 1H, J=8.0 Hz), 7.87-7.90 (m, 2H), 7.76-7.78 (m, 2H), 7.41 (dd, 1H, J=8.0, 11.2 Hz), 6.73 (d, 1H, J=9.6 Hz), 5.86-5.98 (m, 2H), 5.05-5.08 (m, 1H), 3.00-3.15 (m, 1H), 2.80-2.95 (m, 2H), 2.12-2.28 (m, 1H), 2.10-2.20 (m, 2H), 0.97-1.05 (m, 3H), 0.85-0.88 (m, 3H).

Example 19

2-(1-(2-hydroxyethyl)-2,6-dioxopiperidin-3-yl)isoindolin-1,3-dione (S)-2-amino-3-phenylpropanoate 1) 2-(1-(2-hydroxyethyl)-2,6-dioxopiperidin-3-yl)isoindolin-1,3-dione (S)-2-(tert-butoxycarbonylamino)-3-phenylpropanoate 2-(S)-Boc-amino-3-phenylpropanoic acid (265 mg) and 2-(1-(2-hydroxyethyl)-2,6-dioxopiperidin-3-yl)isoindoline-1,3-dione (302 mg) were dissolved in DCM (50 mL). The mixture was stirred on a magnetic stirrer at room temperature. DCC (227 mg) and DMAP (20 mg) were added in one portion and the mixture was allowed to react overnight. Dicyclohexylurea was filtered off. The filter cake washed with DCM several times. The filtrates were combined, washed with brine three times (30 mL/wash), dried over anhydrous magnesium sulfate, and filtered. The solvent is eliminated by rotary evaporation in vacuo. The crude product was purified by silica gel column chromatography (eluted with dichloromethane:acetone=5:2) to yield 522 mg of pure title compound.

2) 2-(1-(2-hydroxyethyl)-2,6-dioxopiperidin-3-yl)isoindolin-1,3-dione (S)-2-amino-3-phenylpropanoate 2-(1-(2-hydroxyethyl)-2,6-dioxopiperidin-3-yl)isoindolin-1,3-dione (S)-2-(tert-butoxycarbonylamino)-3-phenylpropanoate (100 mg) was dissolved in 25% TFA/DCM (10 mL) and stirred on a magnetic strirrer at room temperature. The mixture was allowed to react for 4 hrs. DCM and most of TFA were removed by rotary evaporation in vacuo. The foam obtained was dissolved in DCM (50 mL). The mixture washed with saturated sodium bicarbonate and brine, dried over anhydrous magnesium sulfate, and filtered. 52 mg of a solid was obtained after drying in vacuo. $^1$H NMR (CDCl$_3$, ppm) δ 7.80-7.90 (m, 2H), 7.70-7.80 (m, 2H), 7.10-7.35 (m, 5H), 4.95-5.12 (m, 1H), 4.35-4.45 (m, 1H), 4.15-4.25 (m, 2H), 4.00-4.15 (m, 1H), 3.65-3.72 (m, 1H), 2.95-3.10 (m, 2H), 2.75-2.90 (m, 3H), 2.12-2.20 (m, 1H).

Example 20

2-(1-(2-hydroxyethyl)-2,6-dioxopiperidin-3-yl)isoindolin-1,3-dione nicotinate

The title compound was obtained by the method described in example 19 with nicotinic acid instead of (S)-2-(tert-butoxycarbonylamino)-3-phenylpropanoate. $^1$H NMR (CDCl$_3$, ppm) δ 9.2 (s, 1H), 8.78 (d, 1H, J=4.0 Hz), 8.29 (d, 1H, J=8.0 Hz), 7.87-7.90 (m, 2H), 7.75-7.78 (m, 2H), 7.41 (dd, 1H, J=4.0, 8.0 Hz), 4.97-5.08 (m, 1H), 4.28-4.33 (m, 2H), 4.08-4.16 (m, 2H), 3.30 (s, 2H), 2.97-3.02 (m, 1H), 2.76-2.85 (m, 2H), 2.31 (s, 6H), 2.10-2.14 (m, 1H).

Example 21

2-(1-(2-hydroxyethyl)-2,6-dioxopiperidin-3-yl)isoindolin-1,3-dione N-ethyl-(S)-2-pyrrolidinecarboxylate The title compound was obtained by the preparation method described in example 15 with 2-(1-(2-hydroxyethyl)-2,6-dioxopiperidin-3-yl)isoindolin-1,3-dione (S)-2-pyrrolidinecarboxylate instead of 2-(1-(2-hydroxyethyl)-2,6-dioxopiperidin-3-yl)isoindolin-1,3-dione (S)-2-amino-3-methylbutanoate.

Example 22

2-(1-(4-hydroxybutyl)-2,6-dioxopiperidin-3-yl)isoindoline-1,3-dione

The title compound was obtained by the preparation method described in example 1 by the reaction of 2-(2,6-dioxopiperidin-3-yl)isoindoline-1,3-dione and 4-chlorobutanol. $^1$H NMR (CDCl$_3$, ppm) δ 7.88-7.91 (m, 2H), 7.76-7.78 (m, 2H), 4.95-5.05 (m, 1H), 3.82-3.88 (m, 2H), 3.53-3.60 (m, 2H), 2.94-3.02 (m, 1H), 2.72-2.86 (m, 2H), 2.9-2.20 (m, 1H), 1.64-1.88 (m, 4H).

Example 23

2-(1-(4-hydroxybutyl)-2,6-dioxopiperidin-3-yl)isoindolin-1,3-dione nicotinate

The title compound was obtained by the method described in example 19 in a reaction of nicotinic acid and 2-(1-(4-hydroxybutyl)-2,6-dioxopiperidin-3-yl)isoindoline-1,3-dione. MS (m/e): 436 (M+H).

Example 24

2-(1-(2-hydroxyethyl)-2,6-dioxopiperidin-3-yl)-4-nitroisoindoline-1,3-dione

The title compound was obtained by the method described in example 1 in a reaction of 4-nitro-2-(2,6-dioxopiperidin-3-yl)isoindoline-1,3-dione and chloroethanol. MS (m/e): 347.

Example 25

2-(1-(2-methoxyethyl)-2,6-dioxopiperidin-3-yl)-4-nitroisoindoline-1,3-dione

The title compound was obtained by the method described in example 1 in a reaction of 4-nitro-2-(2,6-dioxopiperidin-3-yl)isoindoline-1,3-dione and 2-methoxyethyl 4-methylbenzenesulfonate. MS (m/e): 361.

Example 26

4-amino-2-(1-(2-hydroxyethyl)-2,6-dioxopiperidin-3-yl)isoindoline-1,3-dione

10% Pd/C (30 mg) was added to a THF solution of 2-(1-(2-hydroxyethyl)-2,6-dioxopiperidin-3-yl)-4-nitroisoindoline-1,3-dione (150 mg). The reaction vessel was pressurized with hydrogen gas at 5 times the atmospheric pressure. After 6 hrs of reaction time, the catalyst was filtered off and solvent was removed by rotary evaporation in vacuo yielding 138 mg of light-yellow solid. MS (m/e): 317.

Example 27

4-amino-2-(1-(2-methoxyethyl)-2,6-dioxopiperidin-3-yl)isoindoline-1,3-dione

10% Pd/C (50 mg) was added to a THF solution of 2-(1-(2-methoxyethyl)-2,6-dioxopiperidin-3-yl)-4-nitroisoindoline-1,3-dione (260 mg). The reaction vessel was pressurized with hydrogen gas at 5 times the atmospheric pressure. After 6 hrs of reaction time, the catalyst was filtered off and solvent was removed by rotary evaporation in vacuo yielding 218 mg of light-yellow solid. MS (m/e): 332 (M+H$^+$).

Example 28

N-(2-(1-(2-methoxyethyl)-2,6-dioxopiperidin-3-yl)-1,3-dioxoisoindolin-7-yl)acetamide Acetic anhydride (0.5 mL) and DMAP (3 mg) were added to a THF solution of 4-amino-2-(1-(2-methoxyethyl)-2,6-dioxopiperidin-3-yl)isoindoline-1,3-dione (50 mg). The reaction mixture was allowed to react for 8 hrs at room temperature. Then, DCM (15 mL) were added and solvents were removed by rotary evaporation in vacuo. The residue was washed with 0.5 N aqueous hydrochloric acid, saturated sodium bicarbonate, and brine, dried over anhydrous magnesium sulfate, and filtered. Pale white solid (38 mg) was obtained after removal of solvent by rotary evaporation in vacuo. MS (m/e): 374 (M+H).

Example 29

4-(dimethylamino)-2-(1-(2-methoxyethyl)-2,6-dioxopiperidin-3-yl)isoindoline-1,3-dione Methyl iodide (0.1 mL) and potassium carbonate powder (300 mg) were added to a DMF solution of 4-amino-2-(1-(2-methoxyethyl)-2,6-dioxopiperidin-3-yl)isoindoline-1,3-dione (50 mg). The reaction mixture was allowed to stir for 48 hrs at room temperature. Then, 30 mL of water was added in for dilution. The mixture was extracted with ethyl acetate (3×20 mL). The organic phases were combined, washed twice with water and once with brine, dried over anhydrous magnesium sulfate and filtered. A crude product was obtained by rotary evaporation in vacuo and was purified further by silica gel column chromatography (eluted with acetic ether eluate:petroleum ether=2:1) to yield 32 mg of pure product. MS (m/e): 360 (M+H$^+$).

Example 30

4-fluoro-2-(1-(2-methoxyethyl)-2,6-dioxopiperidin-3-yl)-4-nitroisoindoline-1,3-dione The title compound was obtained by the method described in example 1 in the reaction of 4-fluoro-2-(2,6-dioxopiperidin-3-yl)isoindoline-1,3-dione and 2-methoxyethyl 4-methylbenzenesulfonate. MS (m/e). MS (m/e): 333.

Example 31

4,5,6,7-tetrafluoro-2-(1-(2-methoxyethyl)-2,6-dioxopiperidin-3-yl)-4-nitroisoindoline-1,3-dione The title compound was obtained by the method described in example 1 by the reaction of 4,5,6,7-tetrafluoro-2-(2,6-dioxopiperidin-3-yl)isoindoline-1,3-dione and 2-methoxyethyl 4-methylbenzenesulfonate. MS (m/e): 387.

Example 32

2-(1-(4-(4-methylbenzene)sulfonyloxybutyl)-2,6-dioxopiperidin-3-yl)isoindolin-1,3-dione 2-(1-(4-hydroxybutyl)-2,6-dioxopiperidin-3-yl)isoindoline-1,3-dione was dissolved in pyridine to which p-toluensulfonyl chloride was previously added. The mixture was reacted at 50° C. for 18 hours. The solvent was eliminated by rotary evaporation in vacuo. Then, 30 mL of saturated sodium bicarbonate solution were added to the residue. The resultant mixture was extracted with ethyl acetate (3×20 mL). Organic phases were combined, washed twice with water and once with brine, dried over anhydrous magnesium sulfate, and filtered. Crude product obtained after rotary evaporation in vacuo was used directly in the next example.

Example 33

2-(1-(4-(diethylamino)butyl)-2,6-dioxopiperidin-3-yl)isoindoline-1,3-dione

The title compound was obtained by the method described in example 9 in the reaction of 2-(1-(4-(4-methylbenzene)sulfonyloxybutyl)-2,6-dioxopiperidin-3-yl)isoindolin-1,3-dione, and diethylamine. MS (m/e): 386(M+H).

What is claimed is:

1. A compound of the formula (I), or an organic or inorganic salt thereof, (I)

[Chemical structure of formula (I): isoindoline-1,3-dione with R¹ substituent on benzene ring, N-linked to 2,6-dioxopiperidin-3-yl with N-(CH₂)ₙ-R² on piperidine nitrogen]

wherein
n is 1, 2, 3, 4, 5 or 6,
R¹ represents from one to four of the same or different substituents selected from F, Cl, Br, $C_{1-4}$ alkyl, OH, $OC_{1-4}$ alkyl, $NO_2$, $NHC(O)C_{1-4}$ alkyl, $NH_2$, $NH(C_{1-4}$ alkyl), $N(C_{1-4}$ alkyl)$_2$;
R² represents $OR^3$, $NR^3R^4$, or $N(R^3)COR^4$; and
R³ and R⁴ represent independently and at each occurrence H or $C_{1-4}$ alkyl.

2. The compound of claim 1, wherein n is 1, 2, or 3.

3. The compound of claim 1, wherein R¹ represents from one to four of the same or different substituents selected from F, $NO_2$, $NH_2$, $NHCH_3$, $NHCH_2CH_3$, $N(CH_3)_2$, $N(CH_2CH_3)_2$, —$NHCOCH_3$.

4. The compound of claim 1, wherein R² represents OH, $OCH_3$, $OCH_2CH_3$, $OCH_2CH_2CH_3$, $OCH(CH_3)_2$, $NH_2$, $NHCH_3$, $NHCH_2CH_3$, $N_{(CH3)2}$, or $N(CH_2CH_3)_2$.

5. A compound of claim 1, wherein the compound is 4-amino-2-(1-(2-methoxyethyl)-2,6-dioxopiperidin-3-yl)isoindoline-1,3-dione.

6. A compound of claim 1, wherein the compound is 4-amino-2-(1-(2-hydroxyethyl)-2,6-dioxopiperidin-3-yl)isoindoline-1,3-dione.

7. A compound of claim 1, wherein the compound is 4-fluoro-2-(1-(2-hydroxyethyl)-2,6-dioxopiperidin-3-yl)isoindoline-1,3-dione; 5-amino -2-(1-(2-hydroxyethyl)-2,6-dioxopiperidin-3-yl)isoindoline-1,3-dione ; or 2-(1-(2-hydroxyethyl)-2,6-dioxopiperidin-3-yl)-4-nitroisoindoline-1,3-dione.

8. A compound of claim 1, wherein the compound is 5-amino-2-(1-(2-methoxyethyl)-2,6-dioxopiperidin-3-yl)isoindoline-1,3-dione; 2-(1-(2-methoxyethyl)-2,6-dioxopiperidin-3-yl)-4-nitroisoindoline-1,3-dione; 2-(1-(2-methoxyethyl)-2,6-dioxopiperidin-3-yl)-4-(methylamino)isoindoline-1,3-dione; 4-(dimethylamino)-2-(1-(2-methoxyethyl)-2,6-dioxopiperidin-3-yl)isoindoline-1,3-dione; 4-fluoro-2-(1-(2-methoxyethyl)-2,6-dioxopiperidin-3-yl)-4-nitroisoindoline-1,3-dione; or 4,5,6,7-tetrafluoro-2-(1-(2-methoxyethyl)-2,6-dioxopiperidin-3-yl)-4-nitroisoindoline-1,3-dione.

9. A compound of claim 1, wherein the compound is 2-(1-(2-hydroxyethyl)-2,6-dioxopiperidin-3-yl)isoindoline-1,3-dione; 2-(1-(2-hydroxyethyl)-2,6-dioxopiperidin-3-yl)-5-nitroisoindoline-1,3-dione; 4,5,6,7-tetrafluoro-2-(1-(2-hydroxyethyl)-2,6-dioxopiperidin-3-yl)isoindoline-1,3-dione; 2-(1-(2-hydroxyethyl)-2,6-dioxopiperidin-3-yl)-4-(methylamino)isoindoline-1,3-dione; or 4-(dimethylamino)-2-(1-(2-hydroxyethyl)-2,6-dioxopiperidin-3-yl)isoindoline-1,3-dione.

10. A compound of claim 1, wherein the compound is 2-(1-(4-hydroxybutyl)-2,6-dioxopiperidin-3-yl)isoindoline-1,3-dione.

11. A compound of claim 1, wherein the compound is 4-amino-2-(1-(2-ethoxyethyl)-2,6-dioxopiperidin-3-yl)isoindoline-1,3-dione; 2-(1-(2-ethoxyethyl)-2,6-dioxopiperidin-3-yl)-4-(methylamino)isoindoline-1,3-dione; or 4-(dimethylamino)-2-(1-(2-ethoxyethyl)-2,6-dioxopiperidin-3-yl)isoindoline-1,3-dione.

12. A compound of claim 1, wherein the compound is 4-amino-2-(2,6-dioxo-1-(2-propoxyethyl)piperidin-3-yl)isoindoline-1,3-dione; or 4-(methylamino)-2-(2,6-dioxo-1-(2-propoxyethyl)piperidin-3-yl)isoindoline-1,3-dione.

13. A compound of claim 1, wherein the compound is 4-(dimethylamino)-2-(1-(3-hydroxypropyl)-2,6-dioxopiperidin-3-yl)isoindoline-1,3-dione; or 4-amino-2-(1-(3-hydroxypropyl)-2,6-dioxopiperidin-3-yl)isoindoline-1,3-dione.

14. A compound of claim 1, wherein the compound is 4-(dimethylamino)-2-(1-(3-methoxypropyl)-2,6-dioxopiperidin-3-yl)isoindoline-1,3-dione; 4-amino-2-(1-(3-methoxypropyl)-2,6-dioxopiperidin-3-yl)isoindoline-1,3-dione; or 5-amino-2-(1-(3-methoxypropyl)-2,6-dioxopiperidin-3-yl)isoindoline-1,3-dione.

15. A compound of claim 1, wherein the compound is 2-(1-(4-(diethylamino)butyl)-2,6-dioxopiperidin-3-yl)isoindoline-1,3-dione.

16. A compound of claim 1, wherein the compound is 4-amino-2-(1-(2-methoxyethyl)-2,6-dioxopiperidin-3-yl)isoindoline-1,3-dione; 4-amino-2-(1-(2-hydroxyethyl)-2,6-dioxopiperidin-3-yl)isoindoline-1,3-dione; 4-fluoro-2-(1-(2-hydroxyethyl)-2,6-dioxopiperidin-3-yl)isoindoline-1,3-dione; 5-amino-2-(1-(2-hydroxyethyl)-2,6-dioxopiperidin-3-yl)isoindoline-1,3-dione; or 2-(1-(2-hydroxyethyl)-2,6-dioxopiperidin-3-yl)-4-nitroisoindoline-1,3-dione; 5-amino-2-(1-(2-methoxyethyl)-2,6-dioxopiperidin-3-yl)isoindoline-1,3-dione; 2-(1-(2-methoxyethyl)-2,6-dioxopiperidin-3-yl)-4-nitroisoindoline-1,3-dione; 2-(1-(2-methoxyethyl)-2,6-dioxopiperidin-3-yl)-4-(methylamino)isoindoline-1,3-dione; 4-(dimethylamino)-2-(1-(2-methoxyethyl)-2,6-dioxopiperidin-3-yl)isoindoline-1,3-dione; 4-fluoro-2-(1-(2-methoxyethyl)-2,6-dioxopiperidin-3-yl)-4-nitroisoindoline-1,3-dione; or 4,5,6,7-tetrafluoro-2-(1-(2-methoxyethyl)-2,6-dioxopiperidin-3-yl)-4-nitroisoindoline-1,3-dione; 2-(1-(2-hydroxyethyl)-2,6-dioxopiperidin-3-yl)isoindoline-1,3-dione; 2-(1-(2-hydroxyethyl)-2,6-dioxopiperidin-3-yl)-5-nitroisoindoline-1,3-dione; 4,5,6,7-tetrafluoro-2-(1-(2-hydroxyethyl)-2,6-dioxopiperidin-3-yl)isoindoline-1,3-dione; 2-(1-(2-hydroxyethyl)-2,6-dioxopiperidin-3-yl)-4-(methylamino)isoindoline-1,3-dione; or 4-(dimethylamino)-2-(1-(2-hydroxyethyl)-2,6-dioxopiperidin-3-yl)isoindoline-1,3-dione; 2-(1-(4-hydroxybutyl)-2,6-dioxopiperidin-3-yl)isoindoline-1,3-dione; 4-amino-2-(1-(2-ethoxyethyl)-2,6-dioxopiperidin-3-yl)isoindoline-1,3-dione; 2-(1-(2-ethoxyethyl)-2,6-dioxopiperidin-3-yl)-4-(methylamino)isoindoline-1,3-dione; or 4-(dimethylamino)-2-(1-(2-ethoxyethyl)-2,6-dioxopiperidin-3-yl)isoindoline-1,3-dione; 4-amino-2-(2,6-dioxo-1-(2-propoxyethyl)piperidin-3-yl)isoindoline-1,3-dione; or 4-(methylamino)-2-(2,6-dioxo-1-(2-propoxyethyl)piperidin-3-yl)isoindoline-1,3-dione; 4-(dimethylamino)-2-(1-(3-hydroxypropyl)-2,6-dioxopiperidin-3-yl)isoindoline-1,3-dione; or 4-amino-2-(1-(3-hydroxypropyl)-2,6-dioxopiperidin-3-yl)isoindoline-1,3-dione; 4-(dimethylamino)-2-(1-(3-methoxypropyl)-2,6-dioxopiperidin-3-yl)isoindoline-1,3-dione; 4-amino-2-(1-(3-methoxypropyl)-2,6-dioxopiperidin-3-yl)isoindoline-1,3-dione; or 5-amino-2-(1-(3-methoxypropyl)-2,6-dioxopiperidin-3-yl)isoindoline-1,3-dione; 2-(1-(4-(diethylamino)butyl)-2,6-dioxopiperidin-3-yl)isoindoline-1,3-dione.

17. A method for preparation of a compound of claim 1 comprising reacting a compound of formula (VI)

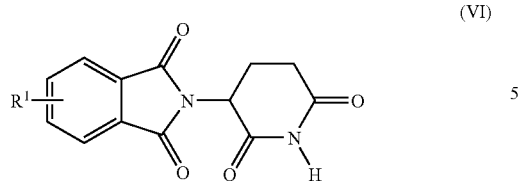
(VI)
with a compound of formula Z—CH$_2$(CH$_2$)$_n$—R$^2$ in the presence of a base, wherein
    the numerical values, atoms and groups represented by n, R$^1$, and R$^2$ are the same as those in claim 1, and
    Z represents Br, or Cl.
* * * * *